(12) United States Patent
Taylor-Papadimitriou et al.

(10) Patent No.: US 7,892,828 B2
(45) Date of Patent: Feb. 22, 2011

(54) METHOD OF IDENTIFYING A MHC CLASS I RESTRICTED T CELL RESPONSE

(75) Inventors: Joyce Taylor-Papadimitriou, Berkhamsted Hertfordshire (GB); Lukas Carl Heukamp, London (GB); Rienk Offringa, Lieden (NL); Cornelis Johanna Maria Melief, Haarlem (NL); Bruce Acres, Straβbourg (FR); Mireille Thomas, Straβbourg (FR)

(73) Assignees: Transgene S.A., Illkirch Graffenstaden (FR); Imperial Cancer Research Technology. Ldt., London (GB)

( * ) Notice: Subject to any disclaimer, the term of this patent is extended or adjusted under 35 U.S.C. 154(b) by 0 days.

(21) Appl. No.: 12/578,499

(22) Filed: Oct. 13, 2009

(65) Prior Publication Data

US 2010/0255501 A1 Oct. 7, 2010

Related U.S. Application Data

(62) Division of application No. 12/042,196, filed on Mar. 4, 2008, now abandoned, which is a division of application No. 11/055,119, filed on Feb. 11, 2005, now abandoned, which is a division of application No. 09/658,621, filed on Sep. 8, 2000, now abandoned.

(60) Provisional application No. 60/187,215, filed on Mar. 3, 2000.

(30) Foreign Application Priority Data

Sep. 8, 1999 (GB) ................................. 9921242.5
Sep. 10, 1999 (EP) ................................. 99402237

(51) Int. Cl.
*C12N 5/08* (2006.01)
*C12N 5/02* (2006.01)
*C12N 5/00* (2006.01)

(52) U.S. Cl. ...................... 435/372.3; 435/375; 435/405

(58) Field of Classification Search ........................ None
See application file for complete search history.

(56) References Cited

U.S. PATENT DOCUMENTS

| | | | |
|---|---|---|---|
| 4,281,061 | A | 7/1981 | Zuk et al. |
| 5,679,641 | A | 10/1997 | Melief et al. |
| 6,248,329 | B1 | 6/2001 | Chandrashekar et al. |
| 6,548,643 | B1 | 4/2003 | McKenzie et al. |
| 6,646,137 | B1 | 11/2003 | Anderson et al. |
| 2002/0052308 | A1 | 5/2002 | Rosen et al. |

FOREIGN PATENT DOCUMENTS

| | | |
|---|---|---|
| EP | 0 369 816 | 5/1990 |
| WO | 96/03502 | 2/1996 |
| WO | 98/17309 | 4/1998 |
| WO | 98/50527 | 11/1998 |
| WO | 00/06723 | 2/2000 |

OTHER PUBLICATIONS

Xiang et al., "Synthetic Peptides Reactive with Anti-Human Milk Fat Globule Membrane Monoclonal Antibodies." Cancer Research, vol. 50, No. 1, Jan. 1, 1990, pp. 89-96.

Apostolopoulos et al., "Anti-MUCQ Antibodies React Directly with MUCc1 Peptides Presented by Class I H2 and HLA Molecules," The Journal of Immunology, vol. 161, 1998, pp. 767-775.

Domenech et al., "Identification of an HLA-A11-Restricted Epitope from the Tandem Repeat Domain of the Epithelial Tumor Antigen Mucin," The Journal of Immunology, vol. 155, 1995, pp. 4766-4774.

Apostolopoulos et al., "MUC1 Peptide Epitopes Associated with Five Different H-2 Class 1 Molecules," European Journal of Immunology, vol. 27, Oct. 1997, pp. 2579-2587.

Nishimori et al., "N-Acetylgalactosamine Glycosylation of MUC1 Tandem Repeat Peptides by Pancreatic Tumor Cell extracts," Cancer Research, vol. 54, Jul. 15, 1994, pp. 3738-3744.

Carmon et al., "Novel Breast-Tumor-Associated MUC1-Derived peptides: Characterization in $D^b$-/-X$\beta$ Microglobulin ($\beta$2m) Null Mice Transgenic for a Chimeric HLA-A2.1$D^b$-$\beta$2 Microblobulin Single Chain," International Journal of Cancer, vol. 85, No. 3, Feb. 1, 2000.

Brossart et al., "Identification of HLA_A2-Restricted T-Cell Epitopes Derived from the MUC1 Tumor Antigen for Broadly Applicable Vaccine Therapies," Blood, vol. 93, No. 12, Jun. 15, 1999.

Agragawal et al., "The Anti-MUC1 Monoclonal Antibody VCP8 Can Be Used to Isolate and Identify Putative Major Histocompatibility Complex Class I Associated Amine Acid," Cancer Research, vol. 58, Nov. 1998, pp. 5151-5156.

Kam et al., " MUC1 Synthetic Peptide Inhibition of Intercellular Adhesion Molecule-1 and MUC1 Binding Requires Six Tandem Repeats," Cancer Research, vol. 58, Nov. 1998, pp. 5577-5581.

Pietersz et al., Definition of MHC-Restricted CTL Epitopes from Non-Variable Number of Tandem Repeat Sequence of MUC1, Vaccine, vol. 18, No. 19, Apr. 2000, pp. 2059-2071.

Agrawal et al., "In Vitro Induction of MUC-1 Peptide-Specific Type 1 T Lymphocyte and Cytotoxic T Lymphocyte Responses from Healthy Multiparous Donors," Cancer Research, vol. 58, Nov. 15, 1998, pp. 2089-2095.

Apostolopoulos et al., "Induction of HLA2-Restricted CTLs to the Mucin 1 Human Breast Cancer Antigen," The Journal of Immunology, vol. 159, 1997, pp. 5211-5218.

Englehard, "Structure of Peptides Associated with MHC Class 1 Molecules", Current Opinion in Immunology, vol. 6, 1994, pp. 12-23.

(Continued)

Primary Examiner—Michail A Belyavskyi
(74) Attorney, Agent, or Firm—Buchanan Ingersoll & Rooney PC

(57) ABSTRACT

Described are peptides and polypeptides derived from the MUC-1 polypeptide which are able to activate Cytotoxic T Lymphocyte (CTL) response, analogues of such peptides and polypeptides nucleotide sequences encoding such peptides and polypeptides and therapeutic uses thereof. Moreover, indications for selecting appropriate minimal antigenic MUC-1 polypeptides with reference to the HLA-type of the patient to be treated or tested are described.

3 Claims, 13 Drawing Sheets

OTHER PUBLICATIONS

Guo et al., "Different Length Peptides Bind to HLA-Aw68 Similarly at Their Ends but Bulge Out in the Middle", Nature, vol. 360 Nov. 1992, pp. 364-366.

Mikayama et al., "Molecular Cloning and Functional Expression of a cDNA Encoding Glycosylation-Inhibiting Factor", PNAS, vol. 90, Nov. 1993, pp. 10056-10060.

Wang et al., "A Single Amino Acid Determines Lysophospholipid Specificity of the S1p1 (EDG1) and LPA1 (EDG2) Phospholipid Growth Factor Receptors", The Journal of Biological Chemistry, vol. 276, No. 52, 2001, pp. 49213-49220.

Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue", The Journal of Cell Biology, vol. 111, Nov. 1990, pp. 2129-2138.

Lazar et al., "Transforming Growth Factor alpha: Mutation of Aspartic Acid 47 and Leucine 48 Results in Different Biological Activities", Molecular and Cellular Biology, vol. 8, No. 3, Mar. 1998, pp. 1247-1252.

Bowie et al., "Deciphering the Message in Protein Sequences: Tolerance to Amino Acid Substitutions", Science, vol. 247, 1990, pp. 1306-1310.

Rammensee et al., "MHC Ligands and Peptide Motifs: First Listing", Immunogenetics, vol. 41, 1995, pp. 178-228.

Lan et al., "Cloning and Sequencing of a Human Pancreatic Tumor Mucin cDNA", The Journal of Biological Chemistry, Sep. 1990, pp. 15294-15299.

```
Met Thr Pro Gly Thr Gln Ser Pro Phe Phe Leu Leu Leu Leu Leu Thr
 1               5                  10                  15
Val Leu Thr Val Val Thr Gly Ser Gly His Ala Ser Ser Thr Pro Gly
            20                  25                  30
Gly Glu Lys Glu Thr Ser Ala Thr Gln Arg Ser Ser Val Pro Ser Ser
            35                  40                  45
Thr Glu Lys Asn Ala Val Ser Met Thr Ser Ser Val Leu Ser Ser His
        50                  55                  60
Ser Pro Gly Ser Gly Ser Ser Thr Thr Gln Gly Gln Asp Val Thr Leu
65                  70                  75                  80
Ala Pro Ala Thr Glu Pro Ala Ser Gly Ser Ala Ala Thr Trp Gly Gln
                85                  90                  95
Asp Val Thr Ser Val Pro Val Thr Arg Pro Ala Leu Gly Ser Thr Thr
                100                 105                 110
Pro Pro Ala His Asp Val Thr Ser Ala Pro Asp Asn Lys Pro Ala Pro
            115                 120                 125
Gly Ser Thr Ala Pro Pro Ala His Gly Val Thr Ser Ala Pro Asp Thr
    130                 135                 140
Arg Pro Ala Pro Gly Ser Thr Ala Pro Pro Ala His Gly Val Thr Ser
145                 150                 155                 160
Ala Pro Asp Asn Arg Pro Ala Leu Gly Ser Thr Ala Pro Pro Val His
                165                 170                 175
Asn Val Thr Ser Ala Ser Gly Ser Ala Ser Gly Ser Ala Ser Thr Leu
            180                 185                 190
Val His Asn Gly Thr Ser Ala Arg Ala Thr Thr Thr Pro Ala Ser Lys
        195                 200                 205
Ser Thr Pro Phe Ser Ile Pro Ser His His Ser Asp Thr Pro Thr Thr
    210                 215                 220
Leu Ala Ser His Ser Thr Lys Thr Asp Ala Ser Ser Thr His His Ser
225                 230                 235                 240
Thr Val Pro Pro Leu Thr Ser Ser Asn His Ser Thr Ser Pro Gln Leu
                245                 250                 255
Ser Thr Gly Val Ser Phe Phe Phe Leu Ser Phe His Ile Ser Asn Leu
            260                 265                 270
Gln Phe Asn Ser Ser Leu Glu Asp Pro Ser Thr Asp Tyr Tyr Gln Glu
        275                 280                 285
```

FIGURE 12A

```
Leu Gln Arg Asp Ile Ser Glu Met Phe Leu Gln Ile Tyr Lys Gln Gly
        290                 295                 300
Gly Phe Leu Gly Leu Ser Asn Ile Lys Phe Arg Pro Gly Ser Val Val
305                     310                 315                 320
Val Gln Leu Thr Leu Ala Phe Arg Glu Gly Thr Ile Asn Val His Asp
                    325                 330                 335
Val Glu Thr Gln Phe Asn Gln Tyr Lys Thr Glu Ala Ala Ser Arg Tyr
                340                 345                 350
Asn Leu Thr Ile Ser Asp Val Ser Val Ser Asp Val Pro Phe Pro Phe
            355                 360                 365
Ser Ala Gln Ser Gly Ala Gly Val Pro Gly Trp Gly Ile Ala Leu Leu
        370                 375                 380
Val Leu Val Cys Val Leu Val Ala Leu Ala Ile Val Tyr Leu Ile Ala
385                 390                 395                 400
Leu Ala Val Cys Gln Cys Arg Arg Lys Asn Tyr Gly Gln Leu Asp Ile
                405                 410                 415
Phe Pro Ala Arg Asp Thr Tyr His Pro Met Ser Glu Tyr Pro Thr Tyr
                420                 425                 430
His Thr His Gly Arg Tyr Val Pro Pro Ser Ser Thr Asp Arg Ser Pro
            435                 440                 445
Tyr Glu Lys Val Ser Ala Gly Asn Gly Gly Ser Ser Leu Ser Tyr Thr
        450                 455                 460
Asn Pro Ala Val Ala Ala Thr Ser Ala Asn Leu
465                     470
```

Recently, Toes et al. (1997, Proc. Natl. Acad. Sci. 94, 14660-14665) have developed an alternative approach based on minimal antigenic polypeptide fragments selection which might be specifically recognized by the CTL. According to said method, the minimal antigenic fragments are expressed in the host cells where they can be associated with MHC-I molecules and then be presented on the cell surface, inducing a specific immune reaction. More specifically, it has been shown that intra-cellular expression of "minigens" encoding very short epitopes (from 7 to 13 amino acids in length) can induce a cellular immune response. Moreover, Whitton et al. (1993, J. of Virology 67, 348-352) have proposed the use of a vector, called "string of beads" construct, which co-expresses several minigens and can induce a synergetic CTL immune response.

Another recent and important use for such polypeptides is in association with soluble complexes of MHC-I, β-2 microglobulin and a fluorescent or otherwise visually detectable reagent. These, so called "Tetramers" (eg, as described in Altman et al, 1996, Science, 274:94-96) can be used to identify by flow cytometry or histology, antigen specific CTL ex vivo.

MUC-1 is a glycosylated mucin polypeptide found on the apical surface of mucin-secreting epithelial cells in various tissues, including breast, lung, pancreas, stomach, ovaries, fallopian tubes, and intestine (Peat et al., 1992, Cancer Res. 52:1954-60—Ho et al., 1993, Cancer Res. 53:641-51). Malignant transformation of breast, ovary, pancreas and probably other epithelial tissues, results in over expression of MUC-1 polypeptide in tumor cells (Hareuveni et al., 1990, Eur. Journ. Biochem. 189:475-86; Layton et al., 1990, Tumor Biol. 11:274-86). In addition, abnormal glycosylation of MUC-1 polypeptide in breast, and probably other MUC-1-expressing tumour cells results in the exposure of tumor-associated antigenic epitopes on the protein core of MUC-1 (Burchell et al., 1987, Cancer Res. 47:5476-82; Devine et al., 1990, J. Tumor Marker Oncol. 5:11-26; Xing et al., 1989, Immun. Cell Biol. 67:183-95) as well as on the glycosyl side chains (Samuel et al., 1990, Cancer Res. 50:4801-8).

Monoclonal antibodies specific for these epitopes have been described which can identify more than 90% of breast and pancreatic tumors. Non major-histocompatibility-complex (MHC) restricted cytotoxic T cell responses to the MUC-1 tumor specific protein epitope by T cells from breast and pancreatic cancer patients have also been reported (Jerome et al., 1991, Cancer Res. 51:2908-16) in addition to MHC restricted, MUC-1-specific CTL (Reddish et al., 1995, Int. J. Cancer 10:817-823). Moreover, proliferation of T cells to purified MUC-1 has been seen (Keydar et al., 1989, Proc. Natl. Acad. Sci. USA 86:1362-6). These various observations suggest that MUC-1 may be an effective target antigen for active immunotherapy in breast, as well as other cancers. Hareuveni et al. (1991, Vaccine 9:618-27) expressed the MUC-1 antigen in vaccinia virus and showed that rat immunized with VV-MUC-1 rejected MUC-1-bearing tumor cells at a rate of 60-80% (Hareuveni et al., 1990, Proc. Natl. Acad. Sci. USA 87:9498-502).

DESCRIPTION OF THE INVENTION

The inventors have now identified epitopes which can be used to induce a MHC class I restricted response which is protective against a tumor challenge. The epitopes are from the MUC1 protein. Since activated T cells express MUC1, these epitopes can also be used to induce an immune response against such T cells or be used to obtain products which are capable of targeting activated T cells.

Thus, the present invention concerns immuno-reactive polypeptides identified from the MUC-1 polypeptide sequence and their uses in cancer therapy and diagnosis. The invention could also be used to follow MUC-1 specific immune responses in patients during the course of disease and/or treatment. The invention also concerns nucleotide sequences encoding these polypeptides, vectors useful for transferring and expressing said nucleotide sequences into target cells, and uses of said nucleotide sequences in cancer gene therapy vaccination and diagnosis.

Accordingly, in a first aspect the present invention relates to polypeptides consisting of or comprising at least one amino acid sequence of at most 20 consecutive amino-acids defined in SEQ ID NO: 1, wherein said polypeptide is different from SEQ ID NO: 2 and is capable of binding with at least one MHC-I molecule.

"Capable of binding with" means that the considered polypeptide is capable to interact and to bind with MHC-I molecules. In a preferred embodiment of the invention, this binding results in cell surface presentation of these polypeptides by MHC class I molecules in order to elicit a specific immune response or for the detection of a specific immune response, eg, by Tetramer analysis (as described, e.g., in Altman et al., 1996, Science 274:94-96).

According to a preferred embodiment, said amino acid sequence is selected from the group consisting of SEQ ID NO: 3 to SEQ ID NO: 33, SEQ ID NO: 65 and SEQ ID NO: 66. Data to explain why these sequences have been selected are shown in FIGS. 1 to 7.

According to a preferred embodiment of the invention, said polypeptide presents at least one of the following properties:

the amino acid sequence is selected from the group consisting of SEQ ID NO:3 to SEQ ID NO:6, SEQ ID NO: 65, SEQ ID NO: 66, and said polypeptide binds the HLA A2 glycoprotein of MHC-I;

the amino acid sequence is selected from the group consisting of SEQ ID NO:7 to SEQ ID NO: 15, and said polypeptide binds the HLA B7 glycoprotein of MHC-I;

the amino acid sequence is selected from the group consisting of SEQ ID NO: 16 to SEQ ID NO: 19, and said polypeptide binds the HLA A3 glycoprotein of MHC-I;

the amino acid sequence is selected from the group consisting of SEQ ID NO: 19 to SEQ ID NO: 21, and said polypeptide binds the HLA A11 glycoprotein of MHC-I;

the amino acid sequence is selected from the group consisting of SEQ ID NO: 22 to SEQ ID NO: 25, and said polypeptide binds the HLA A24 glycoprotein of MHC-I;

the amino acid sequence is selected from the group consisting of SEQ ID NO: 26 to SEQ ID NO: 29, and said polypeptide binds the HLA A1 glycoprotein of MHC-I; and the amino acid sequence is selected from the group consisting of SEQ ID NO: 30 to SEQ ID NO: 33, and said polypeptide binds the HLA B8 glycoprotein of MHC-I.

In a particular preferred embodiment the polypeptide is a peptide that comprises a MHC class I restricted T cell epitope, the epitope being contained in or represented by any one of SEQ ID NO: 1 to 33, 65 or 66, preferably SEQ ID NO: 4, 3, or 5. These latter epitopes lie outside the immunogenic variable non tandem repeat (VNTR) region.

In general, the amino acid sequence present in the polypeptide of the invention may be any stretch of at most 20 contiguous amino acids (such a stretch is in the following referred to as "epitope") of the sequence represented by SEQ ID NO: 1, preferably a sequence represented by any one of SEQ ID NOs: 3 to 33, 65 or 66 below or the amino acid sequence of an epitope present within these sequences (such as the fragments of the sequences shown in the brackets shown below, e.g., for SEQ ID NO: 3 to 5 or for SEQ ID NO: 6, 65 and 66)

```
SEQ ID NO: 3     ALGSTAPPV    (LGSTAPPV)

SEQ ID NO: 4     FLSFHISNL    (LSFHISNL)

SEQ ID NO: 5     TLAPATEPA    (LAPATEPA)

SEQ ID NO: 6     SLSYTNPAV    (SLSYTNPA or LSYTNPAV)

SEQ ID NO: 65    LLLTVLTVV    (LLLTVLTV or LLTVLTVV)

SEQ ID NO: 66    ALGSTTPPA    (LGSTTPPA)
```

In one embodiment the polypeptide of the invention has the same sequence as the "epitope". The peptide typically comprises 1, 2, 3 or more copies of each of 1, 2 or more, or all of the above defined "epitopes".

Typically in the polypeptide, a 'linker' sequence may or may not separate the "epitopes" and/or there may or may not be additional (non-"epitope") sequences at the N terminal or C terminal of the polypeptide. Typically the peptide comprises 1, 2, 3 or more linkers. The linkers are typically 1, 2, 3, 4 or more amino acids in length and may comprise amino acid sequence encoded by a polynucleotide sequence that comprises enzyme restriction sites or amino acids that constitute proteosomal cleavage sites. Thus, in the polypeptide 1, 2 or more, or all of the "epitopes" may be contiguous with each other or separated from each other. The "epitope" sequences may overlap with each other. The polypeptide is typically 8 to 2000 amino acids in length, such as 9 to 1000, 10 to 500, 11 to 200, 12 to 100 or 15 to 50 amino acids.

The peptide may be a natural protein, a fragment thereof, a non-natural protein, or a fusion protein (typically) comprising sequences from different proteins.

The peptide may or may not comprise or be a fragment of MUC1, which fragment may or may not include the MUC1 VNTR. In a preferred embodiment such a fragment only comprises sequences from outside the VNTR. FIG. 12 shows a representation of the MUC1 amino acid sequence in which only a single perfect copy of the tandem repeat sequence is shown by amino acids 129 to 148 inclusive. In a particularly preferred embodiment the polypeptide of the invention comprises fragments of the MUC1 sequence shown in FIG. 12 or in SEQ ID NO: 2, which fragments do not include any sequence from amino acids 97 to 184, e.g. fragments which do not include sequence from amino acids 90 to 190 (as shown in FIG. 12).

SEQ ID NOs: 4, 3 and 5 can be seen at amino acid positions 264 to 272 (inclusive), 167 to 175 (inclusive) and 79 to 87 (inclusive) of FIG. 12. In one embodiment the polypeptide only contains a MUC1 sequence that lies close to the epitopes, such as only sequences from or within positions 258 to 276, 253 to 281, 161 to 179, 156 to 184, 72 to 91 or 67 to 96 of FIG. 12.

The polypeptide may also comprise a sequence which aids the stimulation of a CTL response directed to the epitope. Such sequence may act as adjuvant or may target the polypeptide to antigen presenting cells (APCs) or to compartments in the antigen processing pathway. The sequence may stimulate a T helper response, such as a Th1 response, and thus may comprise a T helper (e.g. Th1) cell epitope. The polypeptide may also comprise the sequence of any of the proteins mentioned herein.

The polypeptide may be free from modifications. In one embodiment the polypeptide is modified, for example by a natural post-translational modification (e.g. glycosylation) or an artificial modification. Thus, the sequence in the polypeptide may or may not comprise the modification(s) that are present when the sequence is expressed in a normal or cancer cell. The polypeptide may comprise the modifications that occur when it is expressed in a eukaryotic (e.g. human) or prokaryotic (e.g. E. coli) cell. In a further embodiment the polypeptide lacks glycosylation.

The modification may provide a chemical moiety (typically by substitution of a hydrogen, e.g. the hydrogen of a C—H bond), such as an amino, acetyl, hydroxy or halogen (e.g. fluorine) group or carbohydrate group. Typically the modification is present on the N or C terminus.

The present invention also relates to analogues of the polypeptides of the invention which are capable of inhibiting the binding of the polypeptide or of an epitope contained in said polypeptide to a T cell receptor either by directly binding to the same T cell receptor or by binding to the same T cell receptor after being processed.

The analogue of the invention is capable of inhibiting the binding of any of the above-mentioned polypeptides (epitopes) to a T cell receptor, either directly or after the analogue is processed. Therefore, certain analogues of the invention can be processed to provide other analogues (that can bind the T cell receptor directly). The term 'analogue' as used here includes both of these types of analogue.

The term 'processed' refers to being processed by the class I antigen presentation pathway (generally this will be hydrolysis, e.g. proteolysis).

Typically the amount of polypeptide (epitope) which can bind the T cell receptor in the presence of the analogue is decreased. This is because the analogue is able to bind the T cell receptor and therefore competes with the epitope for binding to the T cell receptor. The binding of the analogue to the T cell receptor is a specific binding. Generally during the binding discussed above the polypeptide (epitope) or analogue is bound to an MHC class I molecule, such as HLA-A*0201.

The inhibition of binding can be determined using techniques known in the art or any of the techniques or under any of the conditions discussed herein. The T cell receptor used binds specifically to the polypeptide (epitope). T cells with such receptors can be produced by stimulating antigen naive T cells with any of the polypeptides (epitopes) of the invention, for example using the stimulation protocol described in Plebanski et al. (Eur. J. Immunol. 25 (1995), 1783-1787).

Typically an analogue is capable of causing antigen specific functional activation of a T cell which recognises the polypeptide (epitope) (which can be measured using any of the techniques discussed herein). Generally the analogue causes such activation when it is presented to the T cell associated with an MHC class I molecule, such as HLA-A*0201 (for example on the surface of a cell).

The analogue is typically capable of stimulating a MHC class I restricted T cell response directed to the polypeptide (epitope), for example when administered to a human or animal (such as in any of the forms or with any of the adjuvants mentioned herein). Such a response may be protective against a tumor challenge in an animal model or of therapeutic benefit in a human patient.

The analogue typically has a shape, size, flexibility or electronic configuration which is substantially similar to the polypeptide of the invention. It is typically a derivative of the polypeptide.

As well as binding the T cell receptor discussed above the analogue may also be able to bind other specific binding agents that bind the polypeptide (epitope). Such an agent may be HLA-A*0201. The analogue typically binds to antibodies specific for the polypeptide and, thus, inhibits binding of the polypeptide to such an antibody. The analogue is either a peptide or non-peptide or may comprise both peptide and non-peptide portions. Such a peptide or peptide portion may have homology with the polypeptide of the invention.

The analogue may be at least 30% homologous to the polypeptide, preferably at least 50, 70, 80 or 90% and more preferably at least 95%, 97% or 99% homologous thereto, for example over a region of about 20, preferably at least 30, for instance at least 40, 60 or 100 or more contiguous amino acids. Methods of measuring protein homology are well known in the art and it will be understood by those skilled in the art that in the present context, homology is calculated on the basis of amino acid identity (sometimes referred to as "hard homology"). For example the UWGCG Package provides the BESTFIT program which can be used (e.g. on its default setting) to calculate homology (Devereux et al., Nucl. Acids Res. 12 (1984), 387-395).

The homologous peptide typically differs from the epitope present in the polypeptide of the present invention by substitution, insertion or deletion, for example from 1, 2, 3, 4 or more substitutions and/or 1, 2, 3, 4 or more deletions and/or 1, 2, 3, 4 or more insertions over its length. The substitutions are preferably 'conservative'. These are defined according to the following Table. Amino acids in the same block in the second column and preferably in the same line in the third column may be substituted for each other:

TABLE 1

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

Typically the amino acids in an analogue which has homology with the polypeptide which are equivalent to amino acids in the epitope sequence (such as those which contribute to binding the MHC molecule or are responsible for the recognition by the T cell receptor) are the same or are conservatively substituted.

Typically in the analogue the amino acid in position 2 (based on the numbering used for epitopes bound to MHC molecules) is a L or M and/or the amino acid in position 6 is a V and/or the amino acid in position 9 is V or L.

The analogue (including the homologous peptide discussed above) may comprise 1, 2, 3, 4 more non-natural amino acids, for example amino acids with a side chain different from natural amino acids. Generally, the non-natural amino acid will have an N terminus and/or a C terminus. The non-natural amino acid may be an L-amino acid.

Typically the analogue is a peptide which comprises one or more modifications. The sequence of the peptide may be the same as the epitope or homologous peptide discussed above. The modification may be any of the modifications mentioned above which can be present on the polypeptide of the invention.

The modification can be present on any of the amino acids of the polypeptide, such as any of the amino acids responsible for binding the MHC molecule or which contact the T cell receptor during recognition by a T cell.

The analogue is typically designed or selected by computational means and then synthesised using methods known in the art. Alternatively, the analogue can be selected from a library of compounds. The library may comprise peptides which have an HLA-A*0201 binding motif.

The library may be a combinatorial library or a display library, such as a phage display library. The library of compounds may be expressed in the display library in the form of being bound to a MHC class I molecule, such as HLA-A*0201.

Analogues can be selected from the library based on any of the characteristics mentioned above, such as their ability to mimic the binding characteristics of the original epitopes. Thus, they may be selected based on the ability to bind a T cell receptor, HLA-A*0201 or antibody which recognises the epitope. They may be selected based on their ability to cause antigen specific functional activity of a T cell that recognises the epitope (for example using any of the techniques or methods of the invention mentioned herein, e.g. CTL assays, ELISPOT assays or by measuring the production of cytokines inside the T cell).

The analogue which is capable of inhibiting the binding of the polypeptide (epitope) to the T cell receptor after being processed is capable of being processed in the class I antigen processing pathway of a cell to provide a second analogue which can directly inhibit the binding of the polypeptide (epitope) to the T cell receptor.

Such a cell is typically a mammalian or avian cell, such as a human or rodent (e.g. mouse or rat cell). The cell may be a muscle cell or a professional APC (such as a dendritic cell, macrophage, Langerhans cell or B cell). Typically the cell will provide the epitope or analogue on its surface bound to a MHC class I molecule.

The invention also relates to polynucleotides comprising a nucleic acid sequence encoding at least one polypeptide or analogue of the present invention. Based on the amino acid sequences provided with in the present application and by using the genetic code those skilled in the art can easily identify said nucleic acid sequences. According to a preferred embodiment, the nucleic acid sequence of the invention is selected from the group consisting of SEQ ID NO: 34 to SEQ ID NO: 64, and their complementary sequences.

The term "polynucleotide" as used in the scope of the present invention means a DNA and/or RNA fragment, single or double-stranded, linear or circular, natural or synthetic, modified or not (see U.S. Pat. No. 5,525,711, U.S. Pat. No. 4,711,955, U.S. Pat. No. 5,792,608 or EP-A-0 302 175 for modification examples) defining a fragment or a portion of a nucleic acid, without size limitation. It may be, inter alia, a genomic DNA, a cDNA, an mRNA. "Polynucleotides" and "nucleic acids" are synonyms with regard to the present invention. The nucleic acid may be in the form of a linear polynucleotide, and preferably in the form of a plasmid. A wide range of plasmids is commercially available and well known by one skilled in the art. These available plasmids are easily modified by the molecular biology techniques (Sambrook et al., 1989, Laboratory Manual, Cold Spring Harbor Laboratory Press, Cold Spring Harbor, N.Y.). Plasmids derived from pBR322 (Gibco BRL), pUC (Gibco BRL), pBluescript (Stratagene), pREP4, pCEP4 (Invitrogen) and also p Poly (Lathe et al., 1987, Gene 57, 193-201) are illustrative of these modifications. According to the invention, the nucleic acid can be a naked polynucleotide (Wolff et al., Science 247 (1990), 1465-1468) or is formulated with at least one compound such as a polypeptide, preferably viral polypeptides, oligonucleotides or cationic lipids, or cationic polymers which can participate in the uptake of the nucleic acid into the cells (see Ledley, Human Gene Therapy 6 (1995), 1129-1144 for a review) or a protic polar compound (examples are provided below in the present specification or in EP-A-0 890362). "Polynucleotide" also designates nucleic acid of viral origin (viral vector) which encodes at least for the polypeptide of the invention. Such viral vector preferably derives from a virus selected among poxvirus (vaccine virus, MVA, canarypox . . . ), adenovirus, retrovirus, herpes virus, alpha virus, foamy virus or adeno associated virus. Said viral vectors and their uses are widely disclosed in gene therapy literature.

Preferably, said nucleic acid includes at least one therapeutically useful gene sequence that can be transcribed and translated to generate a polypeptide of interest and the elements enabling its expression. The genetic information necessary for expression by a target cell comprises all the elements required for transcription of DNA into RNA and, if necessary, for translation of mRNA into a polypeptide. Transcriptional promoters suitable for use in various vertebrate systems are well known. For example, suitable promoters include viral promoters like RSV, MPSV, SV40, CMV or 7.5 k, vaccinia promoter, inducible promoters, tissue specific promoters, synthetic promoters, etc or combination thereof. The nucleic acid can also include intron sequences, targeting sequences, transport sequences, sequences involved in replication or integration. Said sequences have been reported in the literature and can be readily obtained by those skilled in the art. The nucleic acid can also be modified in order to be stabilized with specific components as spermine.

The polynucleotide of the invention is capable of expressing 1, 2, 3 or more (different) compounds, each of which is a polypeptide or analogue of the invention (for example any combination of a polypeptide and an analogue). The polynucleotide is typically DNA or RNA, and is single or double stranded. The polynucleotide generally comprises 1, 2, 3 or more coding sequences which may be the same or different. At least one of the coding sequences encodes a polypeptide or an analogue of the invention. The coding sequence is typically operably linked to a control sequence capable of providing for expression of the polynucleotide. Thus, typically the polynucleotide comprises 5' and 3' to the coding sequence sequences which aid expression, such as aiding transcription and/or translation of the coding sequence. Typically the polynucleotide comprises a promoter, enhancer, transcription terminator, polyadenylation signal, polyA tail, intron, translation initiation codon or translation stop codon.

The polynucleotide may in particular be capable of expressing a polypeptide or analogue of the invention in a mammalian or avian cell, such as in any of the cells discussed herein. The polynucleotide may furthermore be capable of expressing the polypeptide or analogue in the cellular vector discussed below.

The polynucleotide may form or be part of a vector, such as a plasmid or cosmid vector. In one embodiment the polynucleotide is present in a virus or cellular vector, such as a virus which is capable of stimulating a MHC class I restricted T cell response (e.g. a vaccinia virus).

The introduction or transfer process of an anionic substance of interest into a cell is by itself well known. "Introduction or transfer" means that the polynucleotide is transferred into the cell and is located, at the end of the process, inside said cell or within or on its membrane. It is also called "transfection" or "infection" depending on the nature of the vector.

The invention is therefore further directed to a vector, e.g. of viral or plasmid origin, comprising at least a nucleic acid sequence of the invention.

According to a preferred embodiment, the vector of the invention comprises one or more nucleotide sequences selected from the group consisting of:
  the sequences encoding a polypeptide as defined in (a) in addition to one or more of the sequences encoding a polypeptide as defined in (b), (c), (d), (e), (f) or (g),
  the sequences encoding a polypeptide as defined in (b) in addition to one or more of the sequences encoding a polypeptide as defined in (a), (c), (d), (e), (f) or (g),
  the sequences encoding a polypeptide as defined in (c) in addition to one or more of the sequences encoding a polypeptide as defined in (a), (b), (d), (e), (f) or (g),
  the sequences encoding a polypeptide as defined in (d) in addition to one or more of the sequences encoding a polypeptide as defined in (a), (b), (c), (e), (f) or (g),
  the sequences encoding a polypeptide as defined in (e) in addition to one or more of the sequences encoding a polypeptide as defined in (a), (b), (c), (d), (f) or (g),
  the sequences encoding a polypeptide as defined in (f) in addition to one or more of the sequences encoding a polypeptide as defined in (a), (b), (c), (d), (e) or (g), and
  the sequences encoding a polypeptide as defined in (g) in addition to one or more of the sequences encoding a polypeptide as defined in (a), (b), (c), (d), (e) or (f).

Said constructs are named "string of beads" (Whitton et al. 1993, loc. cit.)

Furthermore, the present invention relates to host cells comprising at least one polynucleotide or at least one vector according to the invention. Preferably such a host cell is a prokaryotic cell or a eukaryotic cell, such as a yeast cell, more preferably an animal cell, most preferably a mammalian cell.

The present invention also relates to a composition (iv) that comprises two or more different compounds wherein each of the compounds is (i) a polypeptide or (ii) an analogue or (iii) a polynucleotide of the invention as defined above.

In the composition (iv) 1, 2, 3, 4, 5 or more different compounds may be present, wherein each of these compounds is (i), (ii) or (iii). Thus, the composition may comprise all the epitopes of the invention (present in the form of the polypeptide of the invention), or instead of any of these epitopes the equivalent analogue. The composition may comprise 1, 2, 3, 4, 5 or more polynucleotides which together are capable of being expressed to provide 1, 2, 3, 4, 5 or more different epitopes, analogues or polypeptides of the invention, or all the epitopes (or instead of any of the epitopes the equivalent analogue) of the invention (e.g. in the form of polypeptide of the invention).

In particular, (i), (ii), (iii) or (iv) are provided for use in a method of vaccination against cancer or for use in a method of immunosuppression. 1, 2, 3, 4, 5, or more different epitopes of the invention (or all of the epitopes of the invention) may be used (or instead of any of these epitopes the equivalent analogue). As discussed above if more than one epitope/analogue is used then the combination of epitopes/analogues may be present in the form of the polypeptide of the invention or in the form of the composition of the invention. Similarly 1, 2, 3, 4, 5 or more different polynucleotides may be used which together are capable of being expressed to provide any of the combinations of epitopes, analogues, polypeptides or compositions mentioned herein.

However, in one embodiment each epitope/analogue or one or more groups of epitopes/analogues within the combination are administered to the host separately or sequentially. The epitopes/analogues in each group are typically together in the form of a single peptide of the invention or in the form of the composition of the invention. Similarly, different polypeptides or polynucleotides of the invention may be administered separately or sequentially, for example polynucleotides capable of expressing individual or groups of epitopes and/or polypeptides and/or analogues and/or compositions.

Thus, the invention provides a combination of 1, 2, 3, 4, 5 or more different epitopes and/or analogues and/or polypeptides and/or compositions and/or polynucleotides of the invention for simultaneous, separate or sequential use in a method of treatment of the human or animal body by therapy, for example in a method of vaccination against cancer or in a method of immunosuppression.

The method of vaccination against cancer or the method of immunosuppression typically leads to a MHC class I restricted T cell response, the T cells of which are specific for an epitope of the invention.

Thus, (i), (ii), (iii), (iv) can be used in a form or manner in which they stimulate such a MHC class I restricted T cell response. Such methods are known in the art. Generally a MHC class I restricted T cell response can be obtained by vaccinating using an appropriate dose, route of administration, adjuvant or delivery system. Thus, the vaccine of the invention may comprise one or more components (for example, as discussed herein in relation to the vaccine of the invention) in addition to (i), (ii), (iii) or (iv). The components of the vaccine may be administered simultaneously, separately or sequentially to the host.

Thus, the invention also provides a vaccine comprising (i), (ii), (iii) or (iv), which vaccine is capable of stimulating a MHC class I restricted T cell response directed to an epitope (polypeptide) of the invention. Typically such a vaccine comprises an adjuvant or delivery system which stimulates a MHC class I restricted T cell response.

The adjuvant may be capable of causing or augmenting a MHC class II restricted T cell (typically CD4) response which is favourable to the production of a MHC class I restricted T cell response, such as a Th1 response. Thus, the adjuvant may comprise a MHC class II restricted T cell epitope (or a precursor which can be processed in vivo to provide such an epitope). The adjuvant may be a cytokine, such as a cytokine which stimulates a MHC class I restricted T cell response or favourable MHC class II restricted T cell response (e.g. IL-2, IL-7, IL-12 or IFN-γ). The adjuvant may be, for example, CFA (Golding and Scott, Ann. N.Y. Acad. Sci. 754 (1995), 126-137), a muramyl dipeptide (e.g. of a mycobacterial cell wall), monophosphoryl lipid A, lipopolysaccharide (e.g. from *B. abortus*), liposomes, SAF-1 (Golding and Scott, Ann. N.Y. Acad. Sci. 754 (1995), 126-137), a saponin (e.g. Quil A), keyhole limpet hemocyanin, yeast TY particle, beta 2-microglobulin or mannan (e.g. oxidised mannan).

The delivery system is typically capable of providing (i), (ii), (iv) or an epitope or analogue expressed from (iii) or (iv) to an APC, such as a professional APC.

As mentioned above the particular route of administration used may aid the stimulating of a MHC class I restricted T cell response and, thus, (i), (ii), (iii), (iv) or the vaccine of the invention may be provided in a form suitable for administering by such a route. Intraperitoneal or intravenous routes are preferred. In one embodiment these substances are delivered by biolistic means.

Generally a low dose of antigen favours the development of a MHC class I restricted T cell response. Thus, in the method a suitable low dose of a compound of the invention can be given. The vaccine may be provided in an amount and concentration that is suitable for administering to provide an appropriate low dose. In one embodiment (iv) is administered in the form of "naked DNA".

The invention also relates to a composition, preferably a pharmaceutical composition, which is particularly useful for the delivery of polynucleotides of the invention to cells or tissues of a subject in the scope of a gene therapeutic method, especially in case of cancer treatment. The term "gene therapy method" is preferably understood as a method for the introduction of a polynucleotide into cells either in vivo or by introduction into cells in vitro followed by re-implantation into a subject. "Gene therapy" in particular concerns the case where the polynucleotide is expressed in a target tissue, especially tissue comprising cell expressing MHC-I molecules.

Preferably, the composition, in particular pharmaceutical composition, furthermore comprises a pharmaceutically acceptable carrier or diluent. The carrier or diluent is non toxic to recipients at the dosages and concentrations employed. Representative examples of carrier or diluent for injectable solutions include water, isotonic saline solutions which are preferably buffered at the physiological pH (such as phosphate buffered saline or Tris-buffered saline), mannitol, dextrose, glycerol and ethanol, as well as polypeptides or protein such as human serum albumin. This carrier or diluent is preferably isotonic, hypotonic or weakly hypertonic and has a relatively low ionic strength. Furthermore, it may contain any relevant solvents, aqueous or partly aqueous liquid carriers comprising sterile, pyrogen-free water, dispersion media, coatings, and equivalents. The pH of the pharmaceutical preparation is suitably adjusted and buffered.

The invention more particularly pertains to a composition, in particular pharmaceutical composition, comprising at least one of the complexes described above and also incorporating at least one adjuvant capable of improving the transfection capacity of said complex. Adjuvants may be selected from the group consisting of a chloroquine, protic polar compounds such as propylene glycol, polyethylene glycol, glycerol, EtOH, 1-methyl L-2-pyrrolidine or their derivatives, or aprotic polar compounds such as dimethylsulfoxide (DMSO), diethylsulfoxide, di-n-propylsulfoxide, dimethylsulfone, sulfolane, dimethylformamide, dimethylacetamide, tetramethylurea, acetonitrile and their derivatives.

In a preferred embodiment, the polynucleotide which is contained in the composition is a DNA. Other particular embodiments of the invention are compositions, in particular pharmaceutical compositions, wherein said polynucleotide is naked, associated with viral polypeptides or complexed with cationic components, more preferably with cationic lipids. In general, the concentration of polynucleotide in such a composition is from about 0.1 μg/ml to about 20 mg/ml.

The composition, in particular pharmaceutical composition, in accordance with the present invention can be administered into a vertebrate tissue. This administration may be made by intradermal, subdermal, intravenous, intramuscular, intranasal, intracerebral, intratracheal, intraarterial, intraperitoneal, intravesical, intrapleural, intracoronary or intratumoral injection, by means of a syringe or other devices. Transdermal administration is also contemplated, as are inhalation, aerosol routes, instillation or topical application.

According to the present invention, the composition, in particular pharmaceutical composition, can be administered into target tissues of the vertebrate body including those of muscle, skin, brain, lung, liver, spleen, bone marrow, thymus, heart, lymph, bone, cartilage, pancreas, kidney, gall bladder, stomach, intestine, testis, ovary, uterus, rectum, nervous system, eye, gland, connective tissue, blood, etc. In a preferred embodiment, said composition will be administered into tumor.

Administration of such a composition to a patient allows to elicit an immune response based on the activation of cytotoxic lymphocytes by the polypeptides encoded by said nucleotide sequences. The composition of the invention is particularly suitable for the treatment or prevention of MUC-1-expressing cancers, such as breast cancer, ovary cancer, pancreas or lung cancer.

According to a special embodiment, the compositions of the present invention, i.e. containing polypeptide or polynucleotide sequences of the instant invention (see above), is suitable for the treatment or prevention of MUC1-expressing cancers, wherein said treatment or prevention comprises:

a step a) consisting in administering to a patient a composition of the present invention, a step b) consisting in administering to the same patient in need a second composition, wherein said composition is either a composition of the present invention, or a composition containing a MUC-1 polypeptide, or a polynucleotide encoding such a MUC-1 polypeptide, wherein said MUC-1 polypeptide is the full length MUC-1 polypeptide of SEQ ID NO: 2, or a MUC-1 polypeptide as disclosed in U.S. Pat. No. 4,963,848, U.S. Pat. No. 5,053,489, WO 8805054 or U.S. Pat. No. 5,861,381 corresponding to MUC-1 polypeptide presenting varying tandem repeat sequence.

According to this special embodiment, both administration steps a) and b) can be made independently of each other or in the same time. This special embodiment can result in boosting the immune response developed by the treated patient.

According to the invention, the term "cells" includes prokaryote cells and eukaryote cells, yeast cells, plant cells, human or animal cells, in particular mammalian cells. In particular, cancer cells should be mentioned. The invention can be applied in vivo to the interstitial or luminal space of tissues in the lungs, the trachea, the skin, the muscles, the brain, the liver, the heart, the spleen, the bone marrow, the thymus, the bladder, the lymphatic system, the blood, the pancreas, the stomach, the kidneys, the ovaries, the testicles, the rectum, the peripheral or central nervous system, the eyes, the lymphoid organs, the cartilage, the endothelium. In preferred embodiments, the cell will be a muscle cell, a haematopoietic system stem cell or an airways cell, a tracheal or pulmonary cell, or a tumor cell.

The present invention also relates to a process for transferring a nucleic acid into cells wherein said process comprises contacting said cells with at least one polynucleotide according to the invention. This process may be applied by direct administration of said polynucleotide to cells of the animal in vivo, or by in vitro treatment of cells which were recovered from the animal and then re-introduced into the animal body (ex vivo process). In in vitro application, cells cultivated on an appropriate medium are placed in contact with a suspension consisting of polynucleotide of the invention. After an incubation time, the cells are washed and recovered. Introduction of the polynucleotide can be verified (eventually after lysis of the cells) by any appropriate method.

In the case of in vivo treatment according to the invention, in order to improve the transfection rate, the patient may undergo a macrophage depletion treatment prior to administration of the pharmaceutical preparations described above. Such a technique is described in the literature (refer particularly to Van Rooijen et al., 1997, TibTech 15, 178-184).

The present invention further concerns the use of a polypeptide or analogue or a polynucleotide, a vector or a host cell as defined above for the preparation of a composition intended for diagnostic, curative, preventive or vaccination treatment of man or animals, and more specifically for the treatment of cancer.

Moreover, the present invention relates to a diagnostic composition comprising at least one polypeptide as defined above. The use of a polypeptide of the invention in a diagnostic composition is illustrated by the following processes:

a process which enables the detection and eventually the quantification of an antibody directed against said polypeptide consists in (i) contacting with said polypeptide a biological sample susceptible to containing said antibody and (ii) detecting the formation of an immune complex between said antibody and said polypeptide.

a process which enables the detection and eventually the quantification of MUC-1-specific T lymphocytes according to the ELISPOT technique (Scheibenbogen et al., 1997, Clinical Cancer Research 3, 221-226); Tetramer analysis (e.g., as described in Altman et al., 1996, Science 274:94-96) or other techniques which allow the identification of specific T cells by virtue of specificity of their T cell receptor for the polypeptides of this invention.

The methods, compositions, uses of the invention can be used for the treatment of all kinds of cancer the treatment and/or diagnostic of which being related to or dependent on the immune properties of the polypeptides of the invention. The compositions, and uses of the present invention may be desirably employed in humans, although animal treatment is also encompassed by the uses described herein.

The present invention also relates to a T cell receptor which recognizes a polypeptide (epitope) of the invention or a fragment thereof which can recognize the polypeptide (epitope).

The T cell receptor of the invention recognises a polypeptide (epitope) of the invention. The fragment of the T cell receptor typically comprises the extracellular domain. The fragment may be a soluble fragment or a fragment capable of binding to a cell membrane. The T cell receptor or fragment may be modified, such as by any of the modifications described herein in relation to the polypeptide of the invention. The T cell receptor or fragment may be part of a fusion protein.

The T cell receptor or fragment is able to bind an MHC molecule (e.g. HLA-A*0201) that comprises the polypeptide (epitope) in its peptide binding groove. Typically the MHC molecule will be present on the surface of a cell. The T cell receptor or fragment may or may not be able to cause antigen specific functional activity of a T cell upon which they are present. This activity may include cytotoxic activity (such as the killing of the cell that bears the MHC/epitope complex which is recognised) or the secretion of substance (such as IFN-γ) from the T cell. The activity may be measured by CTL assay, ELISPOT assay or by measuring the production of cytokine inside the T cell.

The T cell receptor may be present in a population (or composition) which comprises 2, 3, 4, 5 or more different T cell receptors of the invention which together recognise any of the combinations of a polypeptide or analogue of the invention.

Furthermore, the present invention relates to a T cell which comprises a T cell receptor according to the invention.

Such a T cell is preferably a MHC class I restricted cell, and is typically a CD8 T cell, although in one embodiment it is a MHC class I restricted CD4 cell. Generally when the T cell receptor of the T cell recognises the epitope antigen specific functional activity of the cell occurs (such as the functional activity mentioned above). The T cell may be an antigen naive or antigen experienced T cell. The T cell may be of a cell line, such as an immortalised cell line. The T cell may have been fused with another cell, which may or may not be a T cell.

The T cell is typically obtained from a host, such as a naive host, a host that has cancer or a host that has been immunised with a MUC1 based immunogen, such as any of the polypeptides, analogues or polynucleotides mentioned herein. The T cell may be replicated in vitro in an antigen specific (typically by contacting with an epitope or analogue of the invention) or a non-antigen specific manner. Thus, the invention provides a T cell of the invention that has been produced by replication in vitro.

The invention also provides a product that selectively binds a T cell receptor of the invention, typically in a reversible manner Such a product is generally able to inhibit the binding of a polypeptide (epitope) of the invention (e.g. bound to an MHC molecule) to the T cell receptor. The product is typically able to cause antigen specific functional activity of a T cell with the T cell receptor of the invention.

The product typically comprises (a) an MHC molecule, or fragment thereof, comprising a polypeptide (epitope) or analogue of the invention in its peptide binding groove, or (b) an analogue of (a) which is capable of inhibiting the binding of (a) to a T cell receptor of the invention.

The MHC molecule of (a) is generally a class I molecule (e.g. HLA-A*0201). Such molecules comprise an α chain and a β chain. The fragment may comprise only the extracellular domain of the MHC molecule. The fragment may or may not be capable of binding a cell membrane.

(b) may comprise a protein which has homology with a naturally occurring a chain (or a fragment thereof) and/or a protein which has homology with a naturally occurring β chain (or a fragment thereof). The naturally occurring α or β chain may be of an HLA-A molecule (e.g. HLA-A*0201). Any of the above homologous proteins or fragments may be present as part of fusion proteins.

(b) is typically a derivative of (a) and, thus, may be made by modifying (a) by any of the modifications mentioned herein.

The product may be designed, made or identified using methods known in the art. Thus, the invention provides use of a polypeptide (epitope or epitope sequence) of the invention to design or identify the product. The product may be designed by computational means or may be identified from a library of compounds.

Thus, the invention also provides a method of identifying a product of the invention comprising contacting a candidate substance with a T cell receptor or fragment of the invention and determining whether the candidate substance binds to the T cell receptor or fragment, the binding of the candidate substance to the T cell receptor or fragment indicating that the substance is such a product.

In the method the product may be present on the surface of a cell, such as a professional APC. The binding may be measured by contacting the candidate substance with a T cell of the invention and determining whether the candidate substance causes antigen specific functional activity of the T cell (such as by any means mentioned herein).

The product may be linked to a cytotoxic agent. In one embodiment the product is an antibody.

In one embodiment 2, 3, 4 or more products are linked together in a multimer and, thus, the invention provides a multimer comprising 2 or more products of the invention. Such a multimer may be used in the same manner as the product is used in the different aspects of the invention and, thus, the term 'product' as used in the context of the other aspects of the invention includes the multimer.

The products in the multimer may be linked by a covalent bond or by non-covalent means. In a preferred embodiment the products are linked by a streptavidin-biotin interaction and, thus, typically the products comprise a biotin portion (typically chemically linked to or in a fusion protein with the product) which allows the products to be linked together by streptavidin.

The multimer generally has a higher binding affinity to the T cell receptor of the invention than the product, and in one embodiment is able to cause more antigen specific functional activity than the product. The multimer may also comprise a detectable label, such as a radioactive or a light detectable (e.g. fluorescent) label. The label may allow the multimer to be sorted by flow cytometry (e.g. when the multimer is bound to a T cell receptor which is present on a T cell of the invention).

The multimer may be a soluble multimer or may be capable of associating with a cell membrane. In one embodiment the multimer is attached to a solid support, such as a microtitre plate.

The invention also provides a cell comprising a product of the invention. The cell may be any of the types of cells mentioned herein, such as a professional APC or T cell. The cell may be capable of stimulating antigen specific functional activation of a T cell of the invention. Thus, the cell may be used to stimulate a MHC class I restricted T cell response in vitro or in vivo, which response is directed to a polypeptide (epitope) of the invention. The cell may, therefore, be used in a method of treatment of the human or animal body by therapy, particularly in a method of treating or preventing cancer.

In one embodiment the cell may be made by providing a polypeptide, analogue, polynucleotide or composition of the invention to a cell which is able to process the polypeptide, analogue, polynucleotide or composition and present them on its surface (under conditions in which such processing occurs).

The invention furthermore provides a method of causing the replication of MHC class I restricted T cells which are specific for a cancer epitope comprising contacting a population of cells which comprises MHC class I restricted T cells with a polypeptide or analogue of the invention under conditions in which the polypeptide or analogue are presented to T cells in the population, or with a product or cell of the invention.

The invention includes use of a T cell of the invention (including a T cell replicated by the above method) in vitro or in vivo to kill a cell which presents the polypeptide (epitope) of the invention. Such a cell is typically a cancer cell, but in one embodiment is a T cell (typically a MUC1 expressing activated T cell). Thus, the invention provides a T cell of the invention, or a cell which has been replicated in the method of the invention for use in a method of treatment of the human or animal body by therapy. In particular for use in a method of preventing or treating cancer or a disease caused by an immune response, such as an inflammatory disorder, autoimmune disease, organ transplant rejection or graft versus host disease.

As mentioned above, the invention also provides a method of identifying a MHC class I restricted T cell response which is based on determining whether MHC class I restricted T cells from a host recognise a polypeptide or analogue of the invention (either of which may be provided by a polynucleotide of the invention), or a product or cell of the invention. In the method the polypeptide or analogue may be in the form of the composition of the invention.

In one embodiment the determination of whether the T cells recognise the polypeptide or analogue is done by detecting a change in the state of the T cells in the presence of the polypeptide or analogue or determining whether the T cells bind the polypeptide or the analogue. The change in state is generally caused by antigen specific functional activity of the T cell after the T cell receptor binds the polypeptide or the analogue. Generally, when binding the T cell receptor the polypeptide or the analogue is bound to an MHC class I molecule, which is typically present on the surface of an APC.

The change in state of the T cell may be the start of or increase in the expression of a substance in the T cells and/or secretion of a substance from the T cell, such as a cytokine (e.g. IFN-γ, IL-2 or TNF-α). Determination of IFN-γ expression or secretion is particularly preferred. The substance can typically be detected by allowing it to bind to a specific binding agent and then measuring the presence of the specific binding agent/substance complex. The specific binding agent is typically an antibody, such as polyclonal or monoclonal antibodies. Antibodies to cytokines are commercially available, or can be made using standard techniques.

Typically the specific binding agent is immobilised on a solid support (and thus the method may based on the ELISPOT assay to detect secretion of the substance). After the substance is allowed to bind the solid support can optionally be washed to remove material which is not specifically bound to the agent. The agent/substance complex may be detected by using a second binding agent which will bind the complex. Typically the second agent binds the substance at a site which is different from the site which binds the first agent. The second agent is preferably an antibody and is labelled directly or indirectly by a detectable label.

Thus, the second agent may be detected by a third agent which is typically labelled directly or indirectly by a detectable label. For example, the second agent may comprise a biotin moiety, allowing detection by a third agent which comprises a streptavidin moiety and typically alkaline phosphatase as a detectable label.

Alternatively, the change in state of the T cell which can be measured may be the increase in the uptake of substances by the T cell, such as the uptake of thymidine. The change in state may be an increase in the size of the T cells, or proliferation of the T cells, or a change in cell surface markers on the T cell.

The change in state may be the killing (by the T cell) of a cell which presents the polypeptide, the analogue or the product of the invention to the T cell (e.g. the killing of the cell of the invention). Thus, the determination of whether the T cells recognise the peptide may be carried out using a CTL assay.

In one embodiment the T cells which are contacted in the method are taken from the host in a blood sample, although other types of samples which contain T cells can be used. The sample may be added directly to the assay or may be processed first. Typically the processing may comprise diluting of the sample, for example with water or buffer. Typically the sample is diluted from 1.5 to 100 fold, for example 2 to 50 or 5 to 10 fold.

The processing may comprise separation of components of the sample. Typically mononuclear cells (MCs) are separated from the sample. The MCs will comprise the T cells and APCs. Thus, in the method the APCs present in the separated MCs can present the peptide to the T cells. In another embodiment only T cells, (in one embodiment only CD8 T cells), can be purified from the sample. PBMCs, MCs and T cells can be separated from the sample using techniques known in the art.

The T cells used in the assay can be in the form of unprocessed or diluted samples, or are freshly isolated T cells (such as in the form of freshly isolated MCs or PBMCs) which are used directly ex vivo, i.e. they are not cultured before being used in the method. However, more typically the T cells are cultured before use, for example in the presence of the polypeptide or the analogue of the invention and, generally, also exogenous growth promoting cytokines During culturing the polypeptide or the analogue are typically present on the surface of APCs, such as the APC used in the method. Pre-culturing of the T cells may lead to an increase in the sensitivity of the method.

The APC which is typically used in the method is from the same host as the T cell or from a different host. The APC can be a non-professional APC, but is typically a professional APC, such as any of the APCs mentioned herein. The APC maybe an artificial APC. The APC is a cell which is capable of presenting the peptide to a T cell. It is typically separated from the same sample as the T cell and is typically co-purified with the T cell. Thus, the APC may be present in MCs or PBMCs. The APC is typically a freshly isolated ex vivo cell or a cultured cell. It may be in the form of a cell line, such as a short term or immortalised cell line. The APC may express empty MHC class I molecules on its surface.

In one embodiment the method identifies a MHC class I restricted T cell response to any of the combinations of a polypeptide or an analogue of the invention discussed above in relation to the composition of the invention. Thus, in the method the T cells can be placed into an assay with the composition of the invention (which comprises the combination of the polypeptide or the analogue which are to be tested). Alternatively, the T cells can be divided and placed into separate assays each of which contains a group of polypeptides or analogues within the combination.

In one embodiment a polypeptide or an analogue per se is added directly to an assay comprising T cells and APCs. As discussed above the T cells and APCs in such an assay could be in the form of MCs.

In one embodiment the polypeptide or the analogue are provided to the APC in the absence of the T cell. The APC is then provided to the T cell, typically after being allowed to present the polypeptide or the analogue on its surface. The polypeptide or the analogue may have been taken up inside the APC and presented, or simply be taken up onto the surface without entering inside the APC.

The duration for which the polypeptide or the analogue are contacted with the T cells will vary depending on the method used for determining recognition of the peptide. Typically the concentration of T cells used is $10^3$/ml to $10^9$/ml, preferably $10^5$/ml to $10^7$/ml. In the case where peptide is added directly to the assay its concentration is typically from 0.1 to 1000 μg/ml, preferably 10 to 100 μg/ml.

Typically the length of time for which the T cells are incubated with the polypeptide or the analogue is from 4 to 24 hours, preferably 6 to 16 hours.

The determination of the recognition of the polypeptide or the analogue by the T cells may be done by measuring the binding the polypeptide or the analogue to the T cells. Typically, T cells which bind the polypeptide can be sorted based on this binding, for example using a FACS machine. The presence of T cells which recognise the polypeptide will be deemed to occur if the frequency of cells sorted using the polypeptide is above a 'control' value (i.e. above the frequency of antigen naive T cells which recognise the polypeptide or the analogue). The frequency of antigen-experienced T cells during a disease state can be up to 2.5% of the total CD8 T cells.

The polypeptide, the analogue, the polynucleotide, the composition, the product or the cell of the invention can be used to detect a MHC class I restricted T cell response to a polypeptide (epitope) of the invention in vitro (such as in a sample from a host) or in vivo. This can be done, for example, by using the method discussed above. The presence of a response generally indicates the presence of a cell which is expressing MUC1, such as a cancer cell or an activated T cell. Thus, the detection of the response may be used to diagnose cancer. Measurement of the level of the response may be used to monitor the severity of the cancer (i.e. the number of cancer cells present in the host), a larger response indicating a more severe cancer.

In the method of diagnosis of the invention the presence or absence of the MHC class I restricted T cell response is typically determined by the method of identifying a MHC class I restricted T cell response discussed above.

The antibodies mentioned herein may be produced by raising antibody in a host animal. Such antibodies will be specific to the peptide or to the substances mentioned above which bind antibodies. The peptide or substances are referred to as the 'immunogen' below. Methods of producing monoclonal and polyclonal antibodies are well-known. A method for producing a polyclonal antibody comprises immunising a suitable host animal, for example an experimental animal, with the immunogen and isolating immunoglobulins from the serum. The animal may therefore be inoculated with the immunogen, blood subsequently removed from the animal and the IgG fraction purified. A method for producing a monoclonal antibody comprises immortalising cells which produce the desired antibody. Hybridoma cells may be produced by fusing spleen cells from an inoculated experimental animal with tumour cells, for example as described in Köhler and Milstein (Nature 256 (1975), 495-497).

An immortalized cell producing the desired antibody may be selected by a conventional procedure. The hybridomas may be grown in culture or injected intraperitoneally for formation of ascites fluid or into the blood stream of an allogenic host or immunocompromised host. Human antibody may be prepared by in vitro immunisation of human lymphocytes, followed by transformation of the lymphocytes with Epstein-Barr virus.

For the production of both monoclonal and polyclonal antibodies, the experimental animal is suitably a goat, rabbit, rat or mouse. If desired, the immunogen may be administered as a conjugate in which the immunogen is coupled, for example via a side chain of one of the amino acid residues, to a suitable carrier. The carrier molecule is typically a physiologically acceptable carrier. The antibody obtained may be isolated and, if desired, purified.

Administration

Any of the polypeptides, analogues or polynucleotides discussed above in any form or in association with any other agent discussed above is included in the termed "vaccination agent" below. An effective non-toxic amount of such a vaccination agent may be given to a human or non-human patient in need thereof. The condition of a patient suffering from a cancer can therefore be improved by administration of such a vaccination agent. The vaccination agent may be administered prophylactically to an individual who does not have a cancer in order to prevent the individual developing cancer.

Thus, the present invention provides the vaccination agent for use in a method of treating the human or animal body by therapy. The invention provides the use of the vaccination agent in the manufacture of a medicament for vaccinating against cancer. Thus, the invention provides a method of vaccinating an individual comprising administering the vaccination agent to the individual.

The vaccination agent is typically administered by any standard technique used for administering vaccines, such as by injection.

Typically after the initial administration of the vaccination agent a booster of the same or a different vaccination agent of the invention can be given. In one embodiment the subject is given 1, 2, 3 or more separate administrations, each of which is separated by at least 12 hours, 1 day, 2, days, 7 days, 14 days, 1 month or more.

The vaccination agent may be in the form of a pharmaceutical composition which comprises the vaccination agent and a pharmaceutically acceptable carrier or diluent. Suitable carriers and diluents include isotonic saline solutions, for example phosphate-buffered saline. Typically the composition is formulated for parenteral, intravenous, intramuscular, subcutaneous, transdermal, intradermal, oral, intranasal, intravaginal, or intrarectal administration.

The dose of vaccination may be determined according to various parameters, especially according to the substance used; the age, weight and condition of the patient to be treated; the route of administration; and the required regimen. A physician will be able to determine the required route of administration and dosage for any particular patient. A suitable dose may however be from 10 µg to 10 g, for example from 100 µg to 1 g of the vaccination agent. These values may represent the total amount administered in the complete treatment regimen or may represent each separate administration in the regimen.

In the case of vaccination agents which are polynucleotides transfection agents may also be administered to enhance the uptake of the polynucleotides by cells. Examples of suitable transfection agents include cationic agents (for example calcium phosphate and DEAE-dextran) and lipofectants (for example Lipofectam™ and Transfectam™).

When the vaccination agent is a polynucleotide which is in the form of a viral vector the amount of virus administered is in the range of from $10^4$ to $10^{12}$ pfu, preferably from $10^7$ to $10^{10}$ pfu (for example for adenoviral vectors), more preferably about $10^8$ pfu for herpes viral vectors. A pox virus vector may also be used (e.g. vaccinia virus), typically at any of the above dosages. When injected, typically 1-2 ml of virus in a pharmaceutically acceptable suitable carrier or diluent is administered.

These and other embodiments are disclosed or are obvious from and encompassed by the description and examples of the present invention. Further literature concerning any one of the methods, uses and compounds to be employed in accordance with the present invention may be retrieved from public libraries, using for example electronic devices. For example the public database "Medline" may be utilized which is available on the Internet. Further internet databases and addresses are known to the person skilled in the art. An overview of patent information in biotechnology and a survey of relevant sources of patent information useful for retrospective searching and for current awareness is given in Berks, TIBTECH 12 (1994), 352-364.

The invention has been described in an illustrative manner, and it is to be understood that the terminology which has been used is intended to be in the nature of words of description rather than of limitation. Obviously, many modifications and variations of the present invention are possible in light of the above teachings. It is therefore to be understood that within the scope of the appended claims, the invention may be practised otherwise than as specifically described. Accordingly, those skilled in the art will recognize, or able to ascertain using no more than routine experimentation, many equivalents to the specific embodiments of the invention described specifically herein. Such equivalents are intended to be encompassed in the scope of the following claims.

All of the above cited disclosures of patents, publications and database entries are specifically incorporated herein by reference in their entirety to the same extent as if each such individual patent, publication or entry were specifically and individually indicated to be incorporated by reference.

BRIEF DESCRIPTION OF THE DRAWINGS

FIG. 12 shows the amino acid sequence of one version of the MUC-1 protein.

Figure 1:
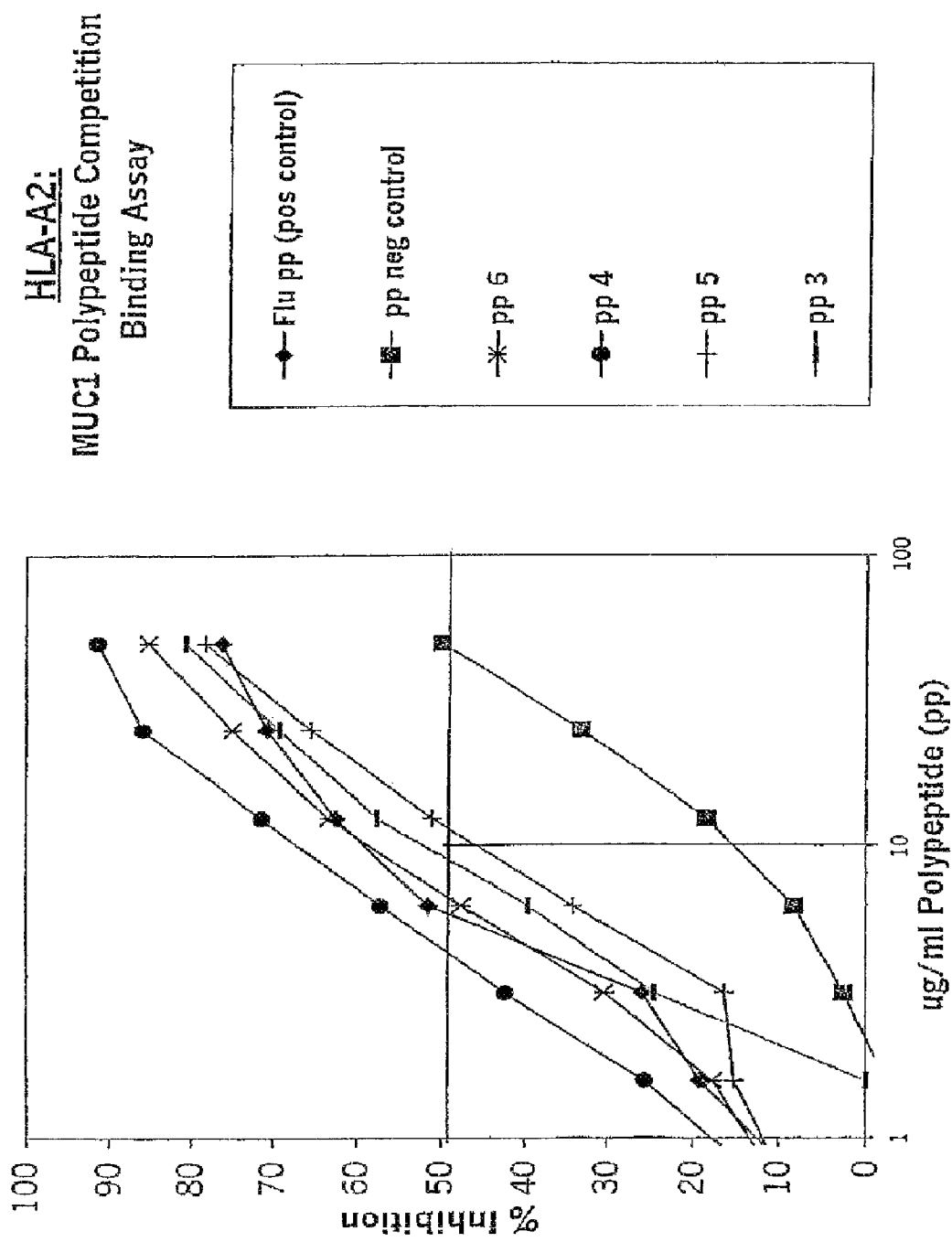
FIGS. 1 to 7 show competition binding data from polypeptides whose sequences are from within the sequence of human MUC-1. Experiments were performed according to the method described in van der Burg et al. (1995, Hum. Immunol. 44:189-198). Polypeptides described as 'pp x' correspond to the SEQ ID NO. For example, pp 27 corresponds to SEQ ID NO 27. In some Figures the competition binding curves of some negative (therefore not claimed) polypeptide sequences are shown to demonstrate the specificity of the competition binding assay.
Figure 2:
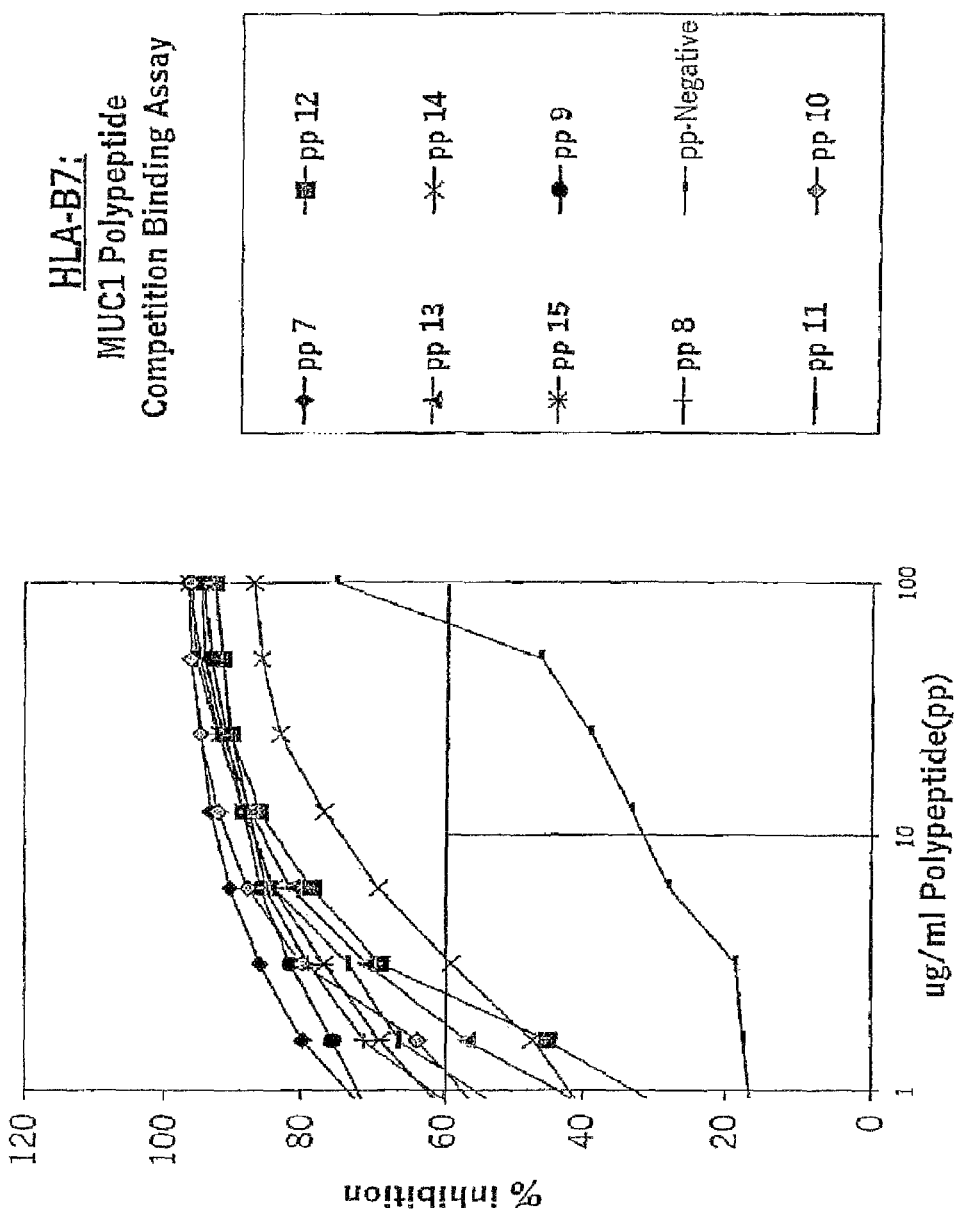
Figure 3:
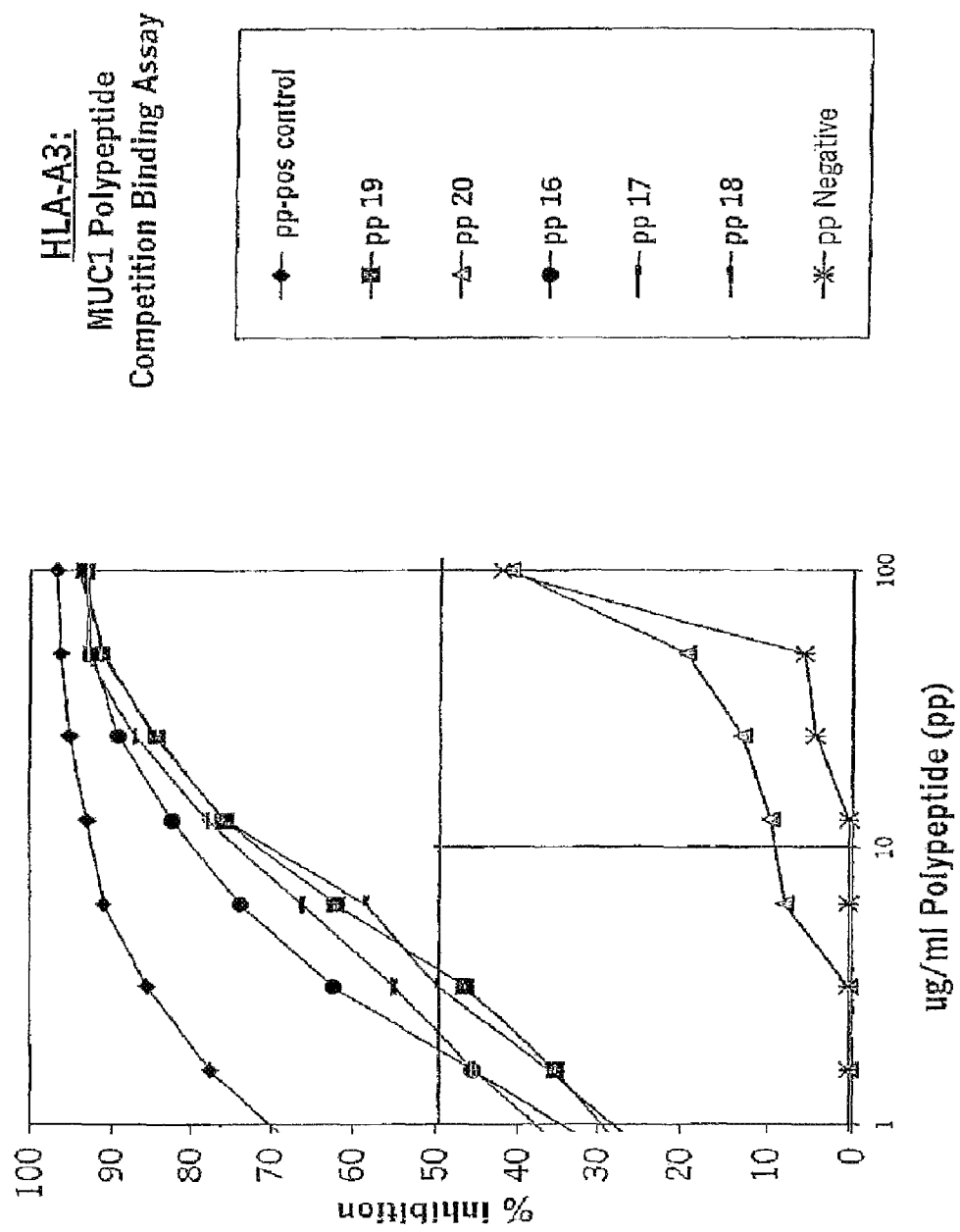
Figure 4:
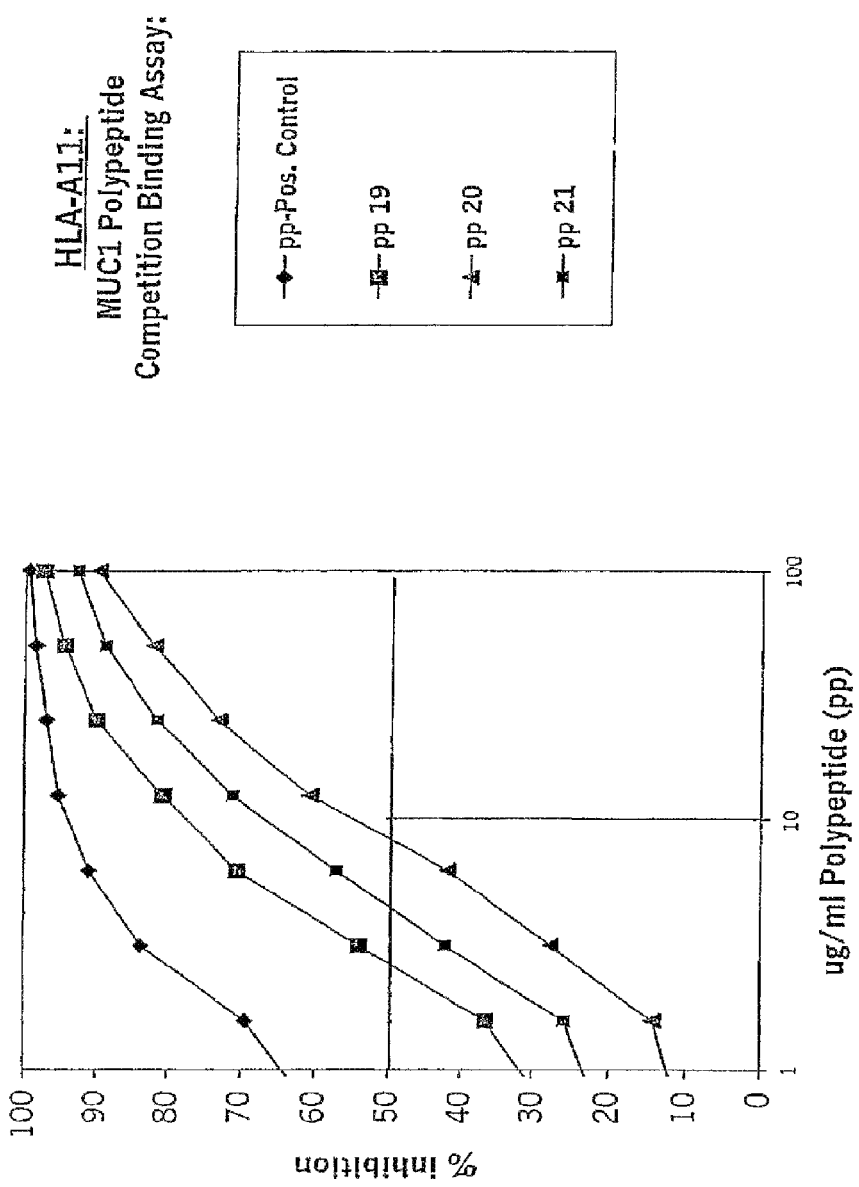
Figure 5:
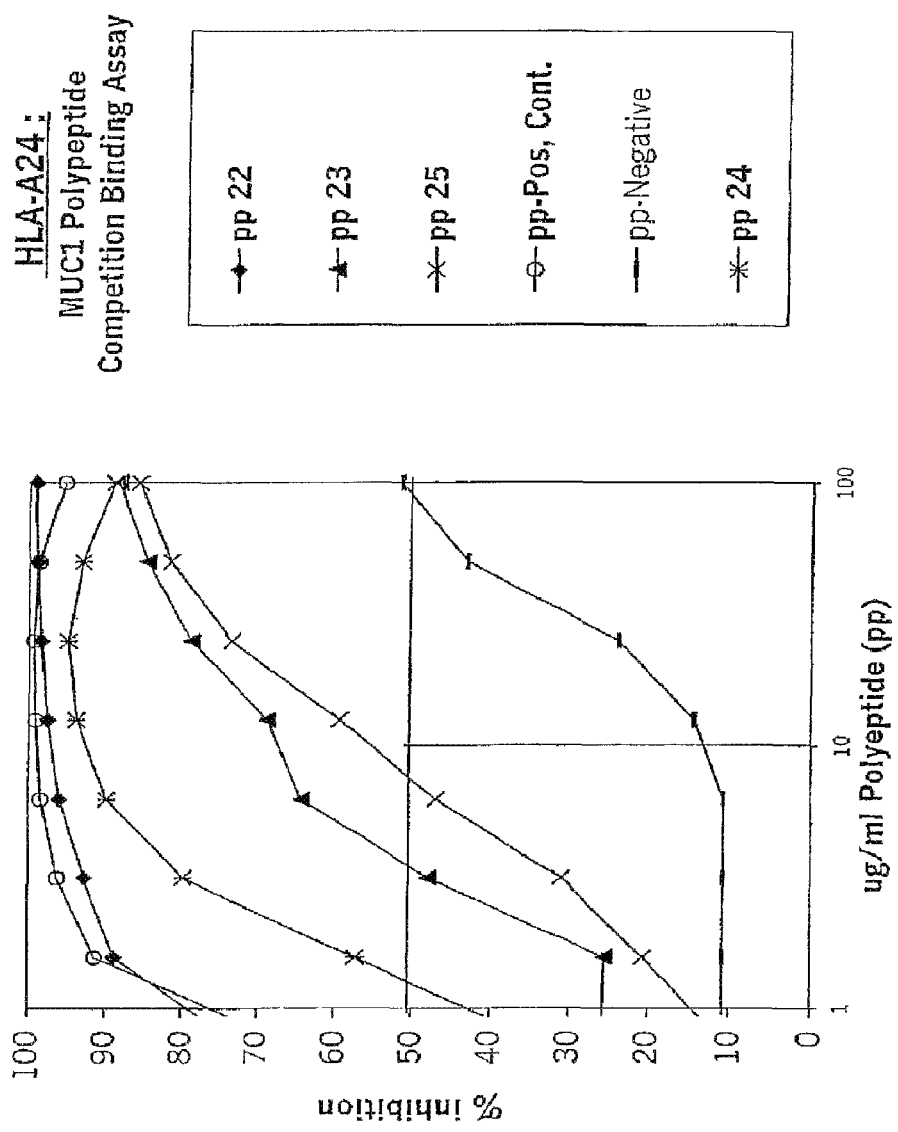
Figure 6:
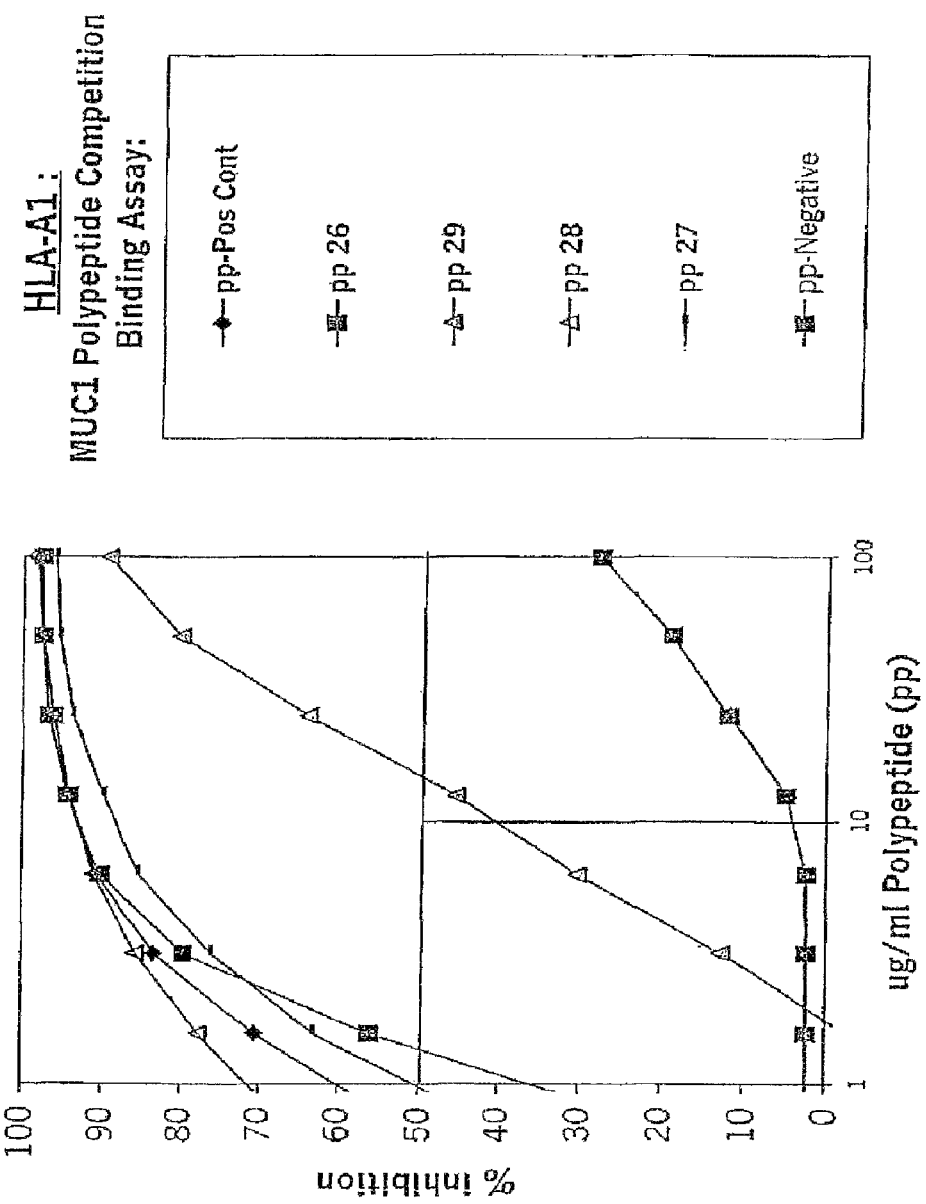
Figure 7:
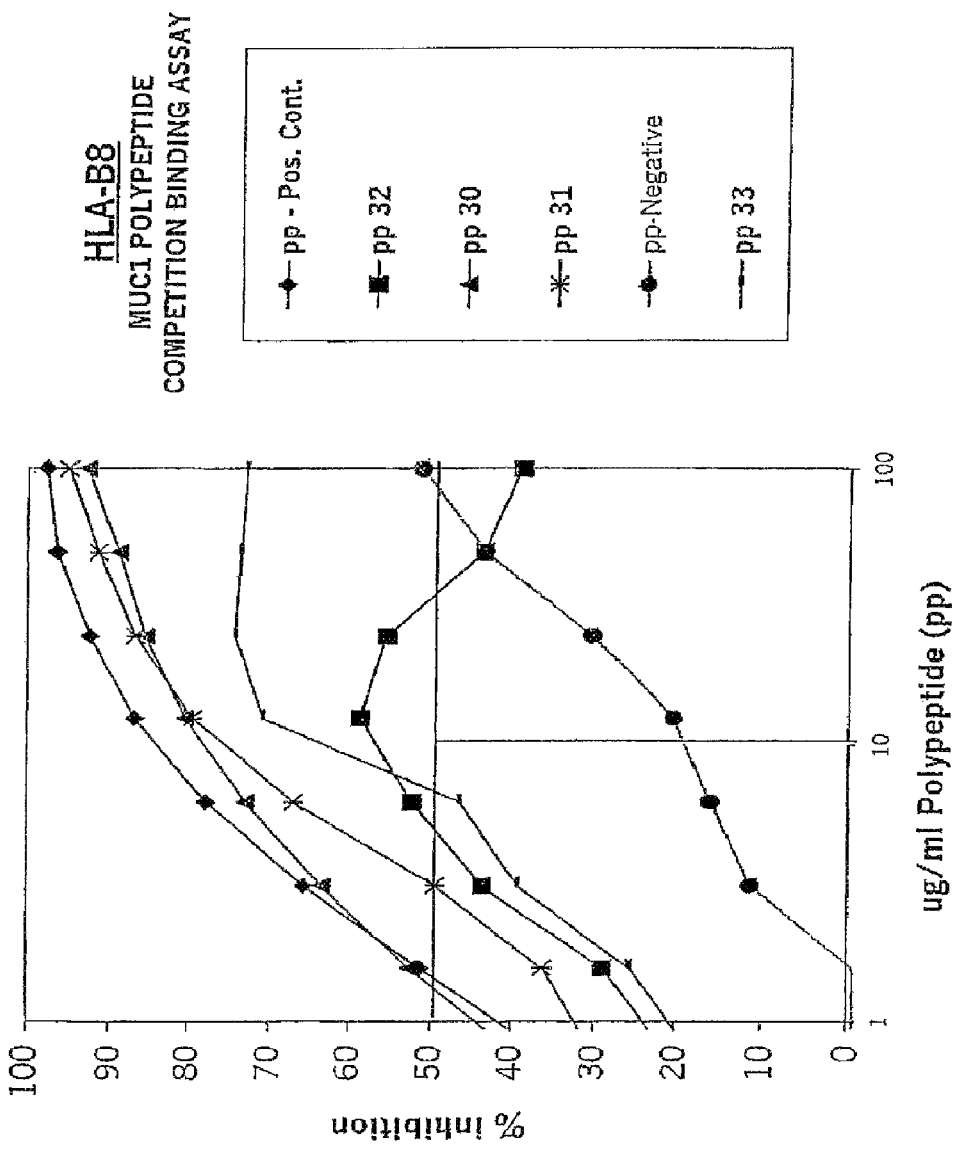

The following examples serve to further illustrate the invention.

EXAMPLES

These examples show:
The identification of MUC-1 polypeptides which bind specifically to molecules of the human Major Histocompatibility Complex I (MHC-I); and
The utility of these polypeptides in a functional bioassay, known as ELISpot (Enzyme Linked Immuno Spot) assay.

Example 1

Competition Binding Assay

INTRODUCTION: Polypeptide fragments 8-13 amino acids long, of proteins produced within a nucleated, vertebrate cell are associated with newly formed cellular proteins of the MHC-I complex. The complex of MHC-I protein and polypeptide fragment are further associated with a protein known as Beta-2 microglobulin. This trimolecular complex is then transported to the cell surface, anchored to the cell membrane and exposed to the extracellular milieu. Thymus-derived, or T lymphocytes of the CD8 category have specific 'antigen' receptors on their cell surface, which recognise the MHC-1-Beta-2-microglobulin-peptide complex. Individual CD8+ T cells or clonal progeny of an individual T cell precursor express on their cell surface antigen receptors which recognise only one (or very few) such polypeptides within the context of the MHC-I-Beta-2-microglobulin-peptide complex. This is known as 'Antigen Specificity' of T lymphocytes. If the polypeptide is derived from a normal or 'self' protein, T lymphocytes are not 'stimulated' due either to the deletion of self-specific T cells from the immune repertoire or due to negative regulation of self-specific immune responses. If, however, the polypeptide is from a pathogenic organism, such as a virus, then specific T cells are activated to proliferate and to become cytotoxic such that CD8 'cytotoxic effector cells' or CTL specifically recognise the infected cell and eliminate that cell in an effort to contain the pathogenic condition. Tumours can also produce 'tumour-specific' protein molecules or modifications of cellular proteins. In those cases, specific CD8 T cells can recognise a tumour cell as pathogenic and eliminate these cells by the same mechanism as is used to eliminate virus-infected cells. Often, the tumour-specific modification of a protein is merely quantitative in that a protein is over-produced in tumour cells. It has been shown that such proteins can also be recognised by specific Cytotoxic T Lymphocytes (CTL). For example see Disis et al., Cancer Research, 54: 1071-1076 (1994); or Barnd et al., Proc Natl Acad Sci USA, 86: 7159-7163 (1989).

It has been shown in numerous publications that the binding of said polypeptides to MHC-I molecules depends upon certain 'motifs' of amino acids at defined positions within the polypeptides. For example, the amino acids Leucine at position 2 and Valine at position 9 of a nine amino acid polypeptide will result in the binding of that polypeptide to HLA-A2. For a review, see Rammensee et al., Immunogenetics, 41: 178-228 (1995). The knowledge of the required amino acid positions had been acquired by the extraction of polypeptides from MHC-I molecules and sequencing them. In addition to the 'anchoring' residues there are various other 'preferred' flanking amino acids, such that a polypeptide can be given a 'rank' of likelihood that it will bind to a particular MHC-I molecule, depending on its sequence. Such ranking of predicted binding of polypeptides can be determined by one of several computer programs. In accordance with the invention, the program 'BIMAS' has been consulted (BioInformatics & Molecular Analysis Section) 'HLA POLYPEPTIDE Binding Predictions' (http://bimas.dcrtmih.gov/molbio/hla_bind/) for predictions of which polypeptides from the human MUC-1 sequence are likely to bind to various HLA types. This, of course, is only a computer prediction and binding must be ascertained with a biochemical assay. Then, whether the polypeptides selected by the binding assay must be tested in a biological assay.

About 200 of the top ranking MUC-1 polypeptides, as predicted by the BIMAS program, predicted to bind to HLA-A1, A2, A3, A11, A24, B7 and B8 were produced (NeoSytem, Strasbourg, France) and were screened for HLA binding by a competitive binding assay. This assay is described in van der Burg et al., Human Immunology, 44:189-198 (1995). Briefly, EBV-transformed B lymphocyte cell lines, of a known HLA-type, are exposed to a polypeptide known to bind to that HLA type. Binding of the polypeptide is determined by flow cytometry using a Fluorescence Activated Cell Sorter. Binding can be envisioned with this apparatus since the polypeptide known to bind is tagged with a flourescene molecule. Thus cells binding the polypeptide become fluorescent. Each polypeptide to be screened for binding is mixed together with the reference fluorescent polypeptide, which is at a constant concentration of 150 nM. The test polypeptide is added at various concentrations and the mixture exposed to the same cells. A test polypeptide is considered 'positive' if the binding of the reference polypeptide is inhibited by 50% at 20 µg/ml or less of the test polypeptide. In FIGS. 1-7 are shown data for the competitive binding of polypeptides deemed, by this assay, to be positive for binding to HLA-A2, B7, A3, A11, A24, A1, and B8 respectively. In each case, binding is compared to a negative control polypeptide, known not to bind to that HLA type and a positive control polypeptide, known to bind to that HLA type. For example, the positive control 'Flu' is a polypeptide with the sequence GILGFVFTL from the influenza virus matrix protein (Scheibenbogen et al. International Journal of Cancer, 71: 932-936 (1997)).

Materials:

EBV-B cell lines were derived by cultivating human Peripheral Blood Mononuclear Cells (PBMC) in filtered culture supernatant which had been used to grow cells from the marmoset line B-958 These cells produce the Epstein Barr Virus. PBMC are cultured for 2-3 days in the presence of 1 µg/ml Cyclosporin A (to inhibit T cell reactivity to the virus) in the B-958 supernatant, then thereafter cultured in fresh culture medium. HLA-typed EBV-transformed human B cell lines were used for all tests HLA types are described in Table 2.

Culture medium was Dulbecco's Modified Eagle's Medium (DMEM)+$5 \times 10^{-5}$ M Beta-Mercaptoethanol (with the addition of 25 mM HEPES buffer for the step of polypeptide detachment and cell washing) plus either 2% or 10% Fetal bovine Serum. All tests were performed in 96 well, V-bottom microtitre plates (PS micro plate). β-2 microglobulin was purchased from Sigma. The buffer for the polypeptide detachment used was:

13.76 g citric acid (M MUC-1 210.14 g/L)
5.43 g $Na_2HPO_4.2H_2O$ (MMUC-1 177.9 g/L)
in 500 ml distilled $H_2O$
pH initially adjusted to pH 4.0, but pH then re-adjusted depending upon which HLA type is being tested (see Table 2).

Dulbecco's Phosphate Buffered Saline (PBS) was purchased as a powder from Sigma. Reference polypeptides labelled with flourescene at the cysteine residue (Table 2) were prepared according to Van de Burg et al., 1995, Hum. Immunol., 44, 189-198. Test polypeptides were purchased from Neo System, Strasbourg or prepared according to standard methods. Positive control polypeptides were purchased from NeoSystem (Strasbourg, France). Details of the polypeptides used are described in Table 2.

Plastics, unless otherwise indicated, were purchased from Corning.

Methods:

Cells were cultivated in Corning T175 flasks in 20 of culture medium (10% FBS). The night before the assay, cells were re-suspended and 10 ml of fresh medium added. The day of the test cells were resuspended, counted, pelleted by centrifugation and resuspended in 5 ml complete medium with 10% FBS. Distribute cells into a 6 well plate, $10^5$ cells per well in 5 ml culture medium. Cells were then cultured for 4 hours at 37°, 5% $CO_2$. During that time polypeptides were prepared by dilution in 600 µg/ml in PBS. Two-fold serial dilutions from 600-4.68 (to have a final dilution of 100 to 0.78 µg/ml in the test plate) were first prepared in a separate 96 well 'polypeptide dilution' plate.

The test plate (96 well, V-bottom) was prepared as follows:

negative control (no polypeptide): 50 µl PBS positive control (reference polypeptide only): 25 µl PBS+ 25 µl Fl-reference polypeptide tests: 25 µl Fl-reference polypeptide at 150 nM (final) then 25 µl of test polypeptides (including positive and negative control polypeptides) at their various dilutions were added. Plates were then placed in a refrigerator in the dark.

After the 4 hour incubation of cells, the following were prepared, on ice:

Two 15 ml conical bottom test tubes containing culture medium with 2% FBS.

One 15 ml conical bottom test tube containing 10 ml culture medium with 2% FBS and including 1.5 µg/ml β-2 microglobulin One 15 ml conical bottom test tube containing 2 ml acid 'peptide detachment' buffer at the pH for the particular HLA type as indicated in Table 2.

Cells in the 5 ml culture medium in the 6 well plate were resuspended and transferred to a 15 ml conical bottom test tube and then centrifuged for 5 minutes at 1500 rpm (500 g). Resuspend the cells in PBS and centrifuge a second time (500 g). Supernatant was removed and 2 ml detachment buffer while on ice. Cells were resuspended by gentle pipetting curing the first 30 seconds of this 2 minute period. After 2 minutes, 14 ml culture medium with 2% FBS was added. Cells are mixed by inverting the tube twice, then centrifuged at 2000 rpm (800 g) for 3 minutes at 4° C. Supernatant was removed and cells resuspended in 14 ml cold culture medium with 2% FBS and centrifugation repeated (3 minutes at 800 g). Supernatant was removed and cells gently resuspended in 14 ml culture medium, 2% FBS and 1.5 µg/ml β-2 microglobulin. One hundred µl cells from this suspension were added to each well of the 96 well plate, which already contained the polypeptides. The plate was wrapped in SARAN™ Wrap and left 24 hours at 4° C. The next day, plates were centrifuged at 1000 rpm (200 g), supernatant removed and cells resuspended in 100 µl PBS containing 0.1% Bovine Serum Albumin (BSA) and 0.02% sodium azide and cells pelleted by centrifugation at 200 g. This step was repeated once more, then cells were resuspended in 1% paraformaldehyde and analysed for fluorescence by a FACSCAN™ (Becton Dickenson, Mountainview Calif.).

The mean fluorescence intensity (MFI) of cells with the fluorescent reference polypeptide but with no competitor polypeptide (positive control) was taken as 0% inhibition. Similarly, the MFI of cells without the fluorescent reference polypeptide (negative control) was taken to be equal to 100% inhibition. Percentage inhibition was calculated as:

$$\% \text{ inhibition}= \left(1 - \frac{(MFI \text{ with test polypeptide}) - (MFI \text{ negative control})}{(MFI \text{ with test polypeptide}) - (MFI \text{ positive control})}\right) \times 100$$

High Affinity Binding was taken to be 50% inhibition at ≦10 µM polypeptide (~10 µg/ml)

TABLE 2

Reference and Positive Control polypeptides used in
the Competition Binding assay

| | | Reference Polypeptide | | | | | |
|---|---|---|---|---|---|---|---|
| Allele tested | elution pH | Sequence (SEQ ID NO:) (origin) | Conc. pmol/µl | Final Conc. nM | Positive Control Polypeptide (SEQ ID NO:) | B-EBV Line | HLA Type |
| A1 | pH 3.1 | YLEPAC*AKY (68) | 183 | 150 | CTELKLSDY (74) (Influenza NP 44-52) | MAR | A01, A02, B08, B27, C01, C07 |
| A2 | pH 3.1 | FLPSDC*FPSV (69) (HBV core 18-27) | 250 | 150 | GILGFVFTL (75) (Influenza matrix 58-66) | JY | A02, B07, C07 |
| A3 | pH 3 | KVFPC*ALINK (70) | 28 et and 20 | | QVPLRPMTYK (76) (HIV nef 73-82) | FRE | A03, A24, B35, B08, C04, C07 |
| A11 | pH 3 | KVFPC*ALINK (70) | 28 et and 20 | 150 | | BVR | A11, B35, C04 |
| A24 | pH 3.1 | RYLKC*QQLL (71) (HIV gp41 583-591) | 66 et and 20 | 150 | AYGLDFYIL (77) (melanoma p15 10-18) | YT2 | A24, B54, C01 |
| B7 | pH 3.1 | APAPAPC*WPL (72) (human p53 84-93) | 29 et and 20 | 150 | RPPIFIRRL (78) (EBNA-3A 379-387) | JY | A02, B07, C07 |
| B8 | pH 3.1 | FLRGRAC*GI (73) (EBNA-3 339-347) | 20 | 150 | YLKDQQLL (79) (HIV gp41 591-598) | MAR | A01, A02, B08, B27, C01, C07 |

Results:

The competition for binding to selected HLA types between serial dilutions of selected peptides and the reference peptides (as described in Table 2) are shown in FIGS. 1-7. Binding of polypeptides, from the sequence of human MUC-1, to HLA-A2, B7, A3, A11, A24, A1 and B8 are shown in FIGS. 1, 2, 3, 4, 5, 6, and 7 respectively. High affinity binding sequences were often, but not always, within the top 20 predicted binding polypeptide sequences as predicted by the BIMAS HLA Peptide Motif program (as described above).

Example 2

ELISpot

The ELISpot is a technique which allows the identification of antigen-specific (in this case, MUC-1-specific) T cell recognition by the detection of antigen induced production of cytokines (IFNγ, TNFα, IL-4, etc. . . . ) following an antigenic stimulation in vitro. More particularly, ELISpot allows the determination of the number of antigen specific T lymphocytes in a population of peripheral blood mononuclear cells (PBMC) (Scheibenbogen et al., 1997, Int. J. Cancer 71-1). In this case, the production of IFNγ produced by CD8+ T cells (CTL) in responses to polypeptides as presented by autologous HLA molecules were examined.

Briefly, in an ELISpot, the cytokines are captured between two specific antibodies. The first antibody, specific for human IFNγ, is adsorbed on a nitrocellulose membrane. Lymphocytes from human blood samples are added to the microtitre wells containing the attached antibody. Antigen, in the form of polypeptides, is also added to the wells. The principal is that polypeptides will attach to cell surface HLA molecules (together with β-2 microglobulin). Polypeptide specific T cells will recognize the complex of the polypeptide:HLA:β-2 µglobulin. Upon recognition of antigen, the T cells become 'activated' to produce cytokines such as IFNγ. Secreted IFNγ is then captured by the antibody which is attached to the nitrocellulose. Cells are washed away leaving behind the areas of secreted IFNγ. These areas are revealed by the second antibody (coupled to biotin) and then by a streptavidin-alkaline phosphatase conjugate. The enzyme substrate hydrolysis by the enzyme leads to a spot appearance. Thus each spot represents the 'fingerprint' of a cytokine producing cell. The tests described below were performed using a commercially available kit (MABTECH, Nacka, Sweden)

Materials

Figure 8:
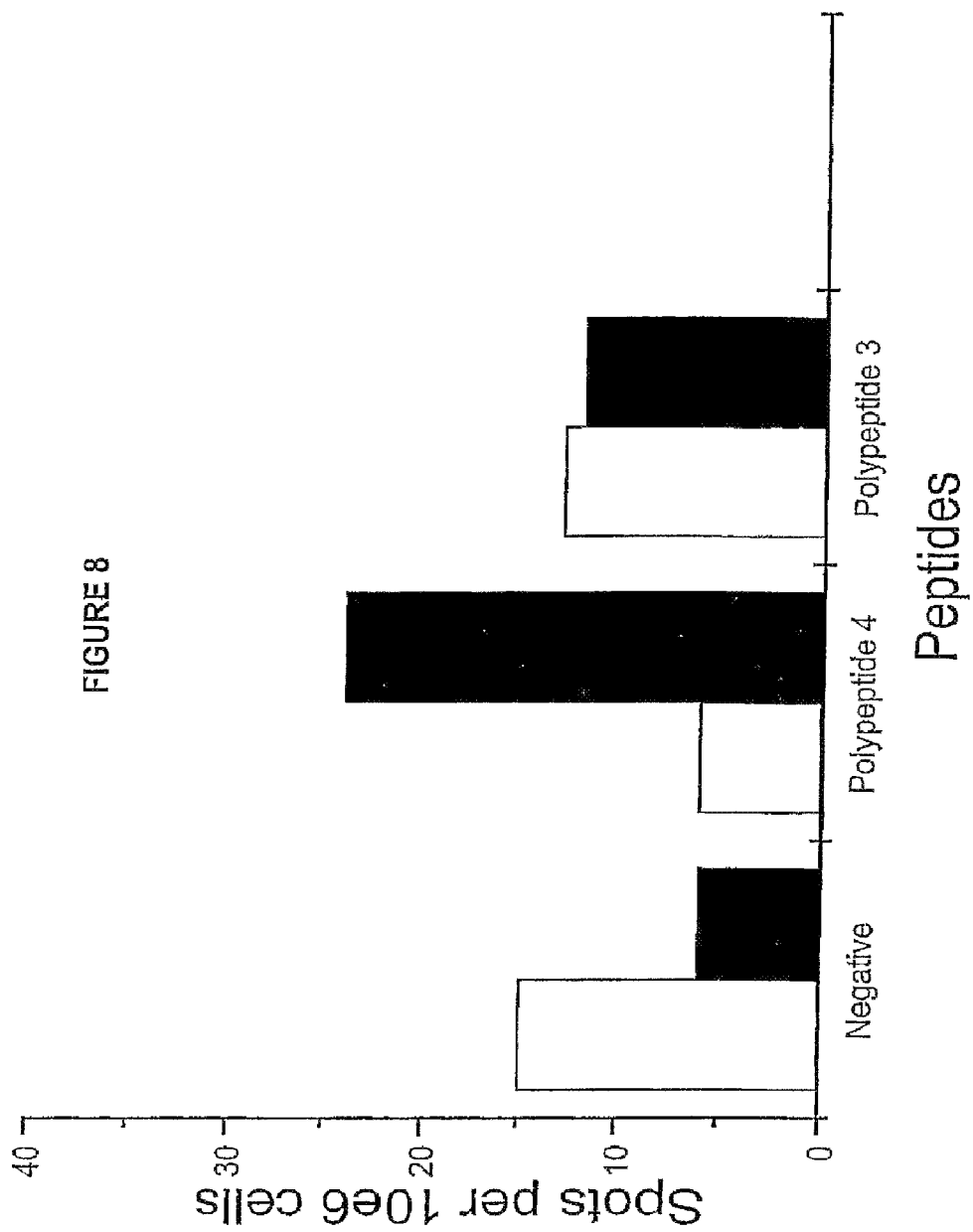
FIGS. 8, 9 and 10 show ELISpot data from three experiments performed with PBMC, from patients immunized with VV-MUC-1-IL2, exposed to polypeptides from this invention. Spots per 10e6 PBMC indicate the number of CD8+ (CTL) T lymphocytes, per million PBMC, which are specific for that polypeptide. Black histograms represent the ELISpot responses of PBMC drawn from the patient 1 weeks after the injection of VV-MUC-1-IL2 (FIG. 8), 4 weeks after injection (FIG. 9) or 4 weeks after the second injection (FIG. 10). The white bars correspond to the ELISpot response of patient PBMC taken before VV-MUC-1 administration (FIG. 8) 5 months after injection (FIG. 9) or before the second injection (FIG. 10).
Figure 9:
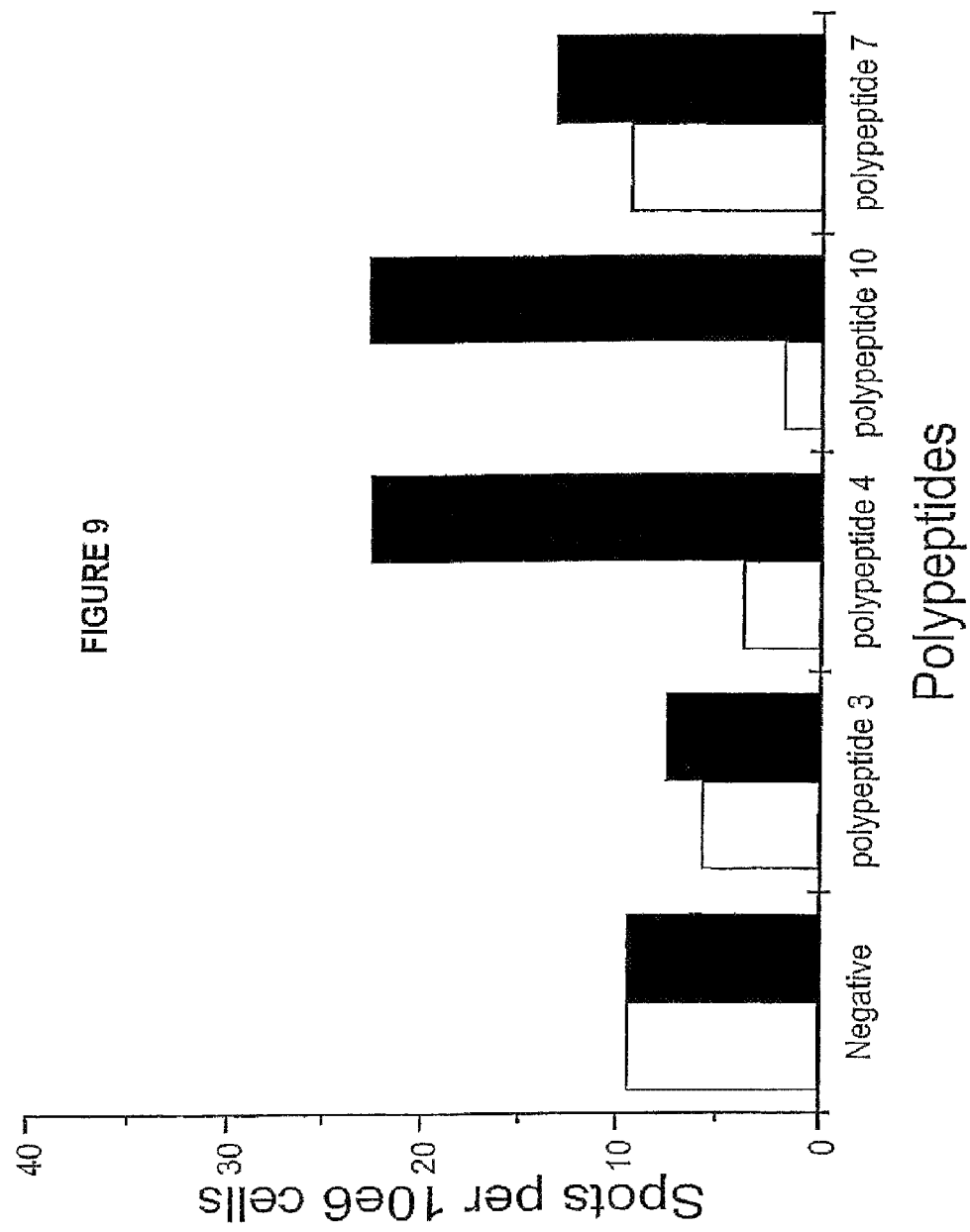
Figure 10:
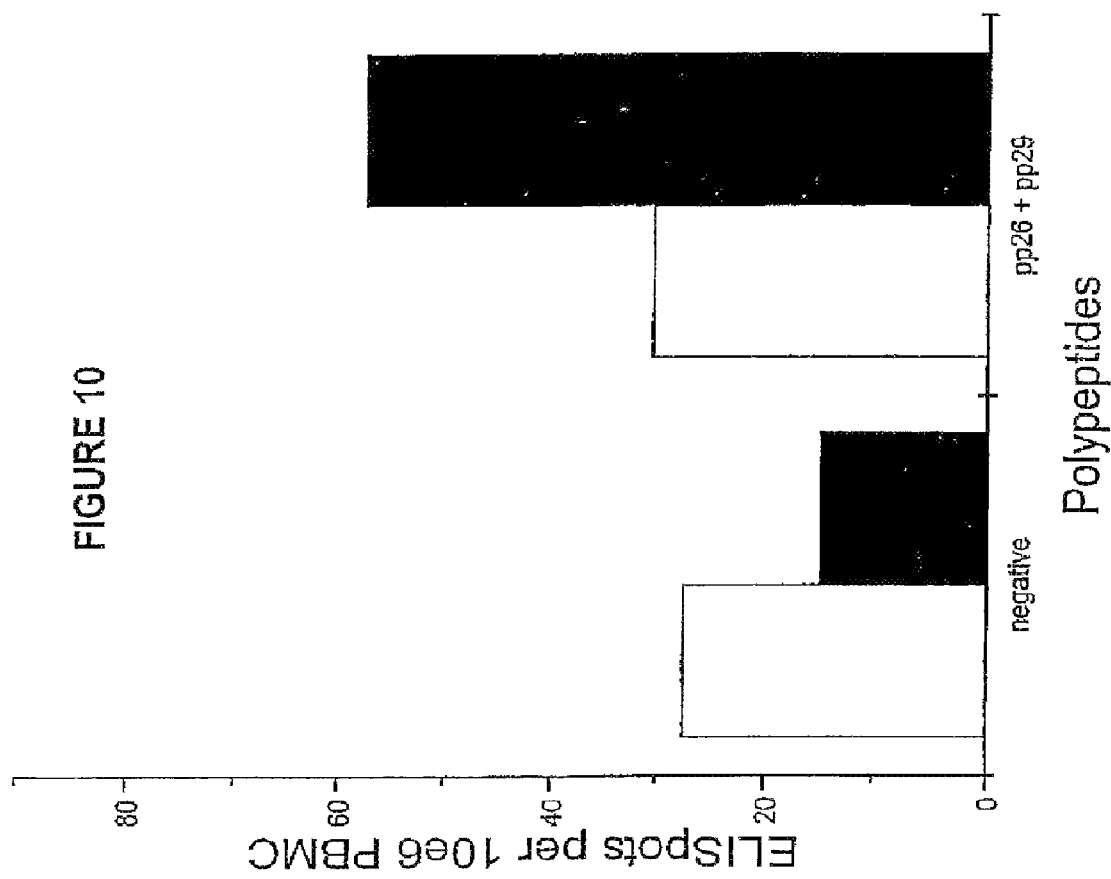

Peripheral Blood Mononuclear Cells:

In FIGS. 8 and 9 patient PBMC (Peripheral Blood Mononuclear Cells) were obtained from breast cancer patients who had participated in a Phase I clinical trial carried out in the Institut Curie, Paris. In FIG. 10, patient PBMC came from prostate cancer patients who had participated in a similar immunotherapy Phase I trial in Los Angeles, USA. In these trials, patients were immunized with a Vaccinia virus construct which expresses, upon infection, the both MUC-1 and IL2. The goal was to generate an immune response to MUC-1 which is an antigen over-expressed on both types of cancers. PBMC were isolated from peripheral blood by Hypaque-Ficol density centrifugation and resulting mononuclear cells frozen in aliquots of 2 to $4 \times 10^6$ cells in a 1 ml volume of culture medium containing 10% DMSO and stored in the vapour phase of liquid nitrogen until use.

TABLE 3

| Patient Identification Code | Cancer | HLA-Type |
|---|---|---|
| Pt#4 SOM | Advanced Breast | HLA-A 01/02; B 44/08 |
| Pt#5 LEC | Advanced Breast | HLA-A 02/24; B 07/44 |
| A002 | Prostate | HLA-A01/26; B38/08 |

Tissue Typing:

Breast cancer patient PBMC was HLA typed by serology and PCR at the Etablissement de Transfusion Sanguine, Strasbourg. Prostate cancer patients' PBMC were HLA typed by PCR at Transgene using the 'ONE LAMDA' HLA typing kit (One Lamda, Canoga Park, Calif., USA)

Polypeptides:

Polypeptides were produced at NeoSytem (Strasbourg, France)

ELISPOT:

The ELISPOT kit was purchased from and used according to the instructions of MABTECH (Nacka, Sweden). The technique was carried out according to the manufacturer's instructions.

Briefly, PBMC were cultured in 96 well microtitre plates for 48 hours in the presence of test or control polypeptides at 5 µg/ml and recombinant IL-2 at 30 units/ml. IFNγ spots were revealed with a second antibody reagent, also specific for Human Interferon gamma, according to the manufacturer's instructions.

Results:

The results from three experiments are shown in FIGS. 8, 9 and 10. Patient PBMC were taken from liquid nitrogen and thawed the day before the ELISpot assay. The controls and the polypeptides (numbered according to their Sequence Identifiers) were added as described above. Duplicate or triplicate wells containing $1-2 \times 10^5$ PBMC were used. The number of spots was determined and is represented as the number of spots per $10^6$ cells.

These data shown in FIG. 8 show that PBMC from patient #4 (who is HLA-A2) are able to respond to the polypeptide of SEQ ID NO: 4 in that PBMC from this patient are stimulated to produce IFNγ in response to the presence of this polypeptide but not in the presence of the negative control polypeptide or polypeptide SEQ ID NO: 3. The response is seen after vaccination (black histograms), but not before (white histograms). In FIG. 9 is shown the results of an experiment in which PBMC from patient #5 (HLA-A2 and B7) are stimulated to produce IFNγ ELISpots upon exposure to polypeptide 4 (SEQ ID NO: 4) and polypeptide 10 (SEQ ID NO: 10) but not to the negative control or to polypeptides 3 or 7. No PBMC from prior to vaccination were available, but the patient's T cell response, as determined by in vitro CD4+ T cell proliferation assay, to a longer (24 aa) MUC-1 polypeptide was discernable only in the weeks following vaccination but was undetectable 5 months afterwards. The transient nature of the T cell responses is verified in FIG. 9 in that only PBMC taken 28 days after vaccination (black histograms) were able to produce ELISpots over background, whereas PBMC taken 5 months after injection produced no ELISpot response to these peptide (white histograms).

These examples demonstrate the value of the invention in the diagnosis of a CD8+ T cell immune response to MUC-1.

The invention could also be used in other diagnostic applications such as Tetramer analysis in which soluble MHC-I, beta-2-microglobulin and polypeptides of this invention are complexed together with a florescent reagent. The complex is then used to fluorescently tag T cells with an antigen receptor specific for that polypeptide. The quantification of the specific T cells is accomplished with a florescence activated flow cytometer and can be done by one practised in the art.

The polypeptides of the invention could also be use in therapeutic or vaccine composition in order to prevent or treat MUC-1-expressing cancers. Polypeptides could be administered alone or complexed with MHC-I and beta-2-microglobulin to stimulate a MUC-1-specific CD8+ (CTL) T cell immune response. The invention could also be used as a DNA-based vector in which olignucleotide sequences coding for the polypeptides of this invention, incorporated into viral or synthetic vector, are used to vaccinate a patient for the treatment or prevention of MUC-1-expressing cancers.

Example 3

Prediction of Peptides that Bind HLA-A*0201

A computer program (D'Amaro et al., Hum. Immunol. 43 (1995), 13-18) was used to scan the MUC1 sequence with two tandem repeats for nine amino acid long peptides complying with the anchor residue motifs for HLA-A*0201. A full set of ninemers with an eight amino acid overlap covering the tandem repeat as well as ninemers in the top 10% of the scoring data for HLA-A*0201 were synthesised (90 peptides in total) by fmoc chemistry with a yield of 5-15 mg.

Example 4

Testing the Synthesised Peptides in a Binding Assay

Peptide binding to HLA-A*0201 was analysed using HLA-A*0201+B lymphoblastoid JY cells in a semi-quantitative competition assay (van der Burg et al. (J. Immunol. 156 (1996), 3308-3314)). The assay is based on competitive binding of two peptides to acid stripped MHC class I molecules on a B cell line (JY). A test peptide competes with a fluorescently labelled reference peptide for the empty class I molecules on the cell surface. Mild-acid-treated JY cells were incubated with 150 nM fluorescein (FL)-labelled reference peptide FLPSDC(-FL)FPSV (SEQ ID NO: 69) and with several concentrations of competitor peptide for 24 hours at 37° C. in the presence of 1.0 m/ml β2-microglobulin. Subsequently, the cells were washed, fixed with paraformaldehyde and analysed by flow cytometry. The mean fluorescence (MF) obtained in the absence of competitor peptide was regarded as maximal binding and equated to 0%; the MF obtained without reference peptide was equated to 100% inhibition. The percentage inhibition was calculated using the formula:

{1−(MF 150 nM reference and competitor peptide− MF no reference peptide)/(MF 150 nM reference peptide−MF no reference peptide)}×100%

The binding capacity of competitor peptides is expressed as the concentration needed to inhibit 50% of binding of the FL-labelled reference peptide (IC50). All peptides were tested several times in two fold dilutions starting with a concentration of 100 µM. The six peptides that showed any significant binding were further analysed. The $IC_{50}$ values of these peptides are shown in the table below together with the value for a flu peptide.

The peptides are defined in terms of the amino acid numbering used in FIG. 12. The tandem repeat can be defined using the restriction enzyme SmaI which cuts at CCCGGG three times in the MUC1 sequence, once either side of the tandem repeat and once in the C-terminus. This leads to the tandem repeat being defined as amino acids 129 to 148 in FIG. 12. The six peptides were analysed further as described below.

| Peptide Position | Amino Acid Sequence | Motif Score * | $IC_{50}$ mM/ml |
|---|---|---|---|
| Flu Matrix$^{58-66}$ | GILGVVFTL (SEQ ID NO: 75) | 54 | <5 |
| MUC1$^{264-272}$ | FLSFHISNL (SEQ ID NO: 4) | 59 | 3-5 |
| MUC1$^{460-468}$ | SLSYTNPAV (SEQ ID NO: 6) | 62 | 5-10 |

-continued

| Peptide Position | Amino Acid Sequence | Motif Score * | IC$_{50}$ mM/ml |
|---|---|---|---|
| MUC1$^{13-21}$ | LLLTVLTVV (SEQ ID NO: 65) | 63 | 6-10 |
| MUC1$^{167-175}$ | ALGSTAPPV (SEQ ID NO: 3) | 64 | 10 |
| MUC1$^{79-87}$ | TLAPATEPA (SEQ ID NO: 5) | 58 | 10-15 |
| MUC1$^{107-115}$ | ALGSTTPPA (SEQ ID NO: 66) | 56 | 25 |

* The algorithm used to define the motif score is described in (D'Amaro et al. (loc. cit.)).

Example 5

Testing the Peptides in a Cytotoxic T Lymphocyte (CTL) Assay

Summary of Assay

To show that the six peptides were functional in vivo, transgenic mice expressing the chimeric protein A*0201K$^b$ (Vitiello et al. (J. Exp. Med. 173 (1991), 1007-1015)) underwent an immunization protocol with a MUC1-derived peptide and T helper epitope formulated with adjuvant. The mice were then sacrificed and the splenocytes restimulated by culturing with peptide-loaded, irradiated LPS-elicited B lymphoblasts. The restimulated cells were separated from the lymphoblasts and used in a CTL assay as effector cells. Effector cells were incubated with Na$^{51}$CrO$_4$ loaded target cells at various E:T ratios and cell killing estimated by measuring the amount of $^{51}$Cr released into the cell supernatant using a gamma radiation counter.

Immunisation of Mice with MUC1-Derived Peptides

Transgenic mice expressing the chimeric protein A*0201K$^b$ (Vitiello et al., loc. cit.) were immunised subcutaneously in the base of the tail with 100 µg of MUC1-derived peptide and 140 µg of H-2I-A$^b$-restricted HBV core antigen-derived T helper epitope (amino acid sequence; TPPAYRPP-NAPIL; SEQ ID NO: 80) (Milich et al., Proc. Natl. Acad. Sci. USA 85 (1988), 1610-1614) emulsified in a 1:1 ratio with Incomplete Freund's Adjuvant (IFA) in a total volume of 200 µl. After a minimum of two weeks, the mice were boosted using the same protocol.

Preparation of LPS-Elicited B Lymphoblasts

Splenocytes from (unimmunized) transgenic mice expressing the chimeric protein A*0201K$^b$ (Vitiello et al., loc. cit.) were prepared 72 h prior to use as stimulator cells. The cells of several mice were pooled and resuspended in IMDM N medium (IMDM (Biowhittaker) supplemented with 2 mM L-glutamine, 8% (v/v) heat inactivated foetal calf serum (FCS), 20 µM 2-mercaptoethanol and 100 IU/ml penicillin) containing 25 µg/ml LPS (Sigma) and 7 µg/ml dextran sulphate (Pharmacia). A 30 ml culture of cellular concentration, 1.5×10$^6$ cells per ml was incubated at 37° C. for 72 h.

Cells were then collected, resuspended in IMDM N, separated on a Ficoll gradient and adjusted to a cellular concentration of 5×10$^6$ cells/ml. Cells were then irradiated for 8 min (the equivalent of 2500 RAD). Cells were then washed once and resuspended in IMDM to a cellular concentration of 40×10$^6$ cells/ml.

Each MUC1 derived peptide, at a concentration of 100 m/ml, was incubated for 1 h at 37° C. with 1 ml LPS-elicited B lymphoblasts. The cells were then washed once and resuspended in IMDM N at a concentration of 10×10$^6$ cells/ml.

Restimulation of Splenocytes from Peptide-Immunized Mice

Two weeks after the final immunization, the mice were sacrificed and the spleens removed. Splenocytes (30×10$^6$ cells in a 9 ml volume of IMDM N medium were restimulated by incubation in complete medium with a 1 ml volume of syngeneic, irradiated LPS-elicited B cell lymphoblasts (such that the ratio of splenocytes to blast cells is 3:1). On day 7 of culture the cells were separated on a Ficoll gradient, resuspended in IMDM N medium and counted to generate a preparation of effector cells of known concentration.

Preparation of Target Cells

The Jurkat-A*0201K$^b$ cell line which is a stable transfectant of a human T cell leukaemia line expressing the product of the HLA-A*0201K$^b$ chimeric gene construct was used as a source of target cells.

Cells growing in log phase were harvested, washed once, counted and 10$^6$ cells transferred to a microfuge tube. The cells were pelleted and resuspended in a 100 µl volume of 1 mCi/ml Na$^{51}$CrO$_4$ solution (Amersham) followed immediately by the addition of a 5 µl volume of 1M HEPES pH 7.0 and gentle mixing of the cell suspension by pipetting. The tubes were incubated for 1 h at 37° C. The cells were then washed four times in IMDM N medium and resuspended in a 25 ml volume of IMDM N medium containing the relevant peptide. After a 20 min incubation the cells were plated out into wells already containing effector CTLs. The final concentration of peptide in each well was 2 µg/ml.

$^{51}$Cr Release Assay

Effector cells, prepared as above, were added in triplicate to wells of a 96 well plate (round bottom wells) such that the resulting ratio of Effector:Target cells was a range from 5:1 to 100:1. For each target cell line tested, six wells containing IMDM N or PBS with 2% (v/v) triton X-100 were prepared as controls to measure the spontaneous and maximal release of $^{51}$Cr respectively.

A 50 µl volume of the preparation of target cells (1000 or 2000 cells depending on preparation and number of effector cells) was then added to each well and the 96 well plates centrifuged for 2 min at 1200 rpm. The plates were then incubated for 6 h at 37° C. The culture supernatants from each well were then harvested using Skaton harvesting frames according to the manufacturer's instructions and the $^{51}$Cr in each supernatant measured using a Wallac gamma counter.

Figure 11:
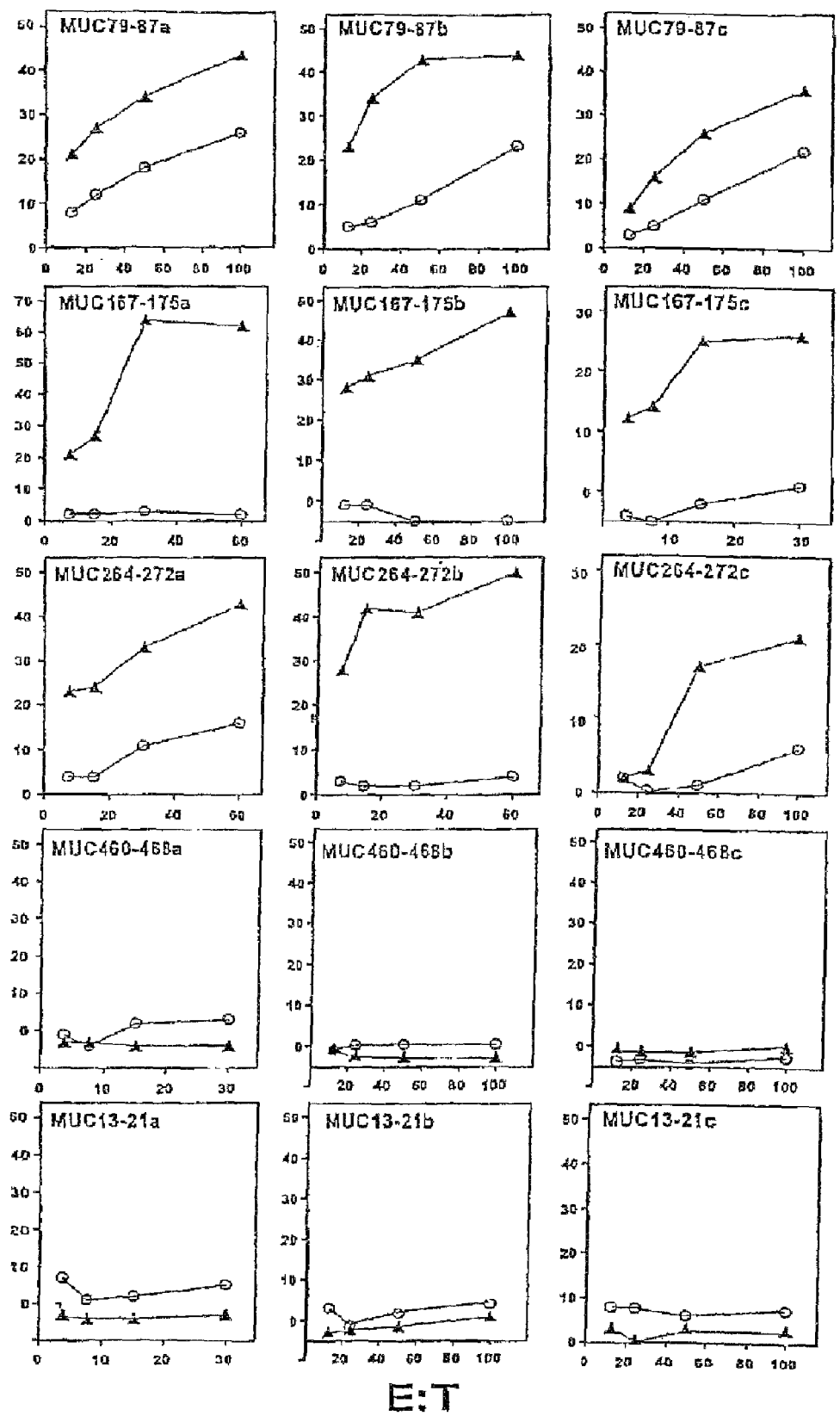
FIG. 11 shows that MUC1 derived HLA-A*0201 binding peptides induce peptide specific cytotoxic CTL responses. A2K$^b$ mice were immunised twice with 100 μg of MUC1 peptide in IFA and 140 μg of Th peptide on day −28 and −14. On day 0 single cell splenocyte suspensions were restimulated in vitro for one week with peptide loaded syngeneic LPS-elicited lymphoblasts and tested for cytotoxicity of peptide loaded Jurkat-A*0201K$^b$. Groups of A2K$^b$ mice were immunised with MUC1 peptides MUC1$^{264-272}$ (FLSFHISNL; SEQ ID NO:4), MUC1$^{460-468}$ (SLSYTNPAV; SEQ ID NO: 6), MUC1$^{13-21}$ (LLLTVLTVV; SEQ ID NO: 65), MUC1$^{167-175}$ (ALGSTAPPV; SEQ ID NO: 3) or MUC1$^{79-87}$ (TLAPATEPA; SEQ ID NO: 5). CTL bulk cultures were tested against Jurkat-A*0201K$^b$ cells loaded with the cognate peptide (filled triangles) or irrelevant influenza matrix control peptide (open circles). Three representative graphs for each peptide are shown. The vertical axis shows % specific lysis.

The data was presented as % age specific $^{51}$Cr release which is defined as 100×([experimental cpm−spontaneous cpm]/[total cpm−spontaneous cpm]) where the experimental value was the average of three test wells, the spontaneous value, the average of six wells containing IMDM N and target cells and the total value is the average of six wells containing 2% (v/v) triton X-100 and target cells. Data is shown for peptides MUC1$^{79-87}$, MUC1$^{167-175}$, MUC1$^{264-272}$, MUC1$^{460-468}$ and MUC1$^{13-21}$ in FIG. 11.

Example 6

Protection Assay

Mice were inoculated subcutaneously with 10$^5$, 5×10$^5$ and 10$^6$ B16-MUC1-A2K$^b$ cells (a melanoma cell line constitutively expressing MUC1 and the chimeric gene product HLA-A*0201K$^b$). Tumour growth was observed 20 days post inoculation and continued until sacrifice of the animal. An inoculation of $5 \times 10^5$ B16-MUC1-A2K$^b$ was defined as the optimal dose for tumour challenge experiments.

To test whether the HLA-A*0201 binding peptides that were previously identified could protect A2K$^b$ transgenic mice (Vitiello et al., loc. cit.) against subsequent tumour challenge with B16-MUC1-A2K$^b$, groups of 6-8 animals were immunised with 100 μg of peptide in IFA in the presence of 140 μg of the H-2I-A$^b$-restricted HBV core antigen-derived T helper epitope (128-140; sequence TPPAYRPP-NAPIL; SEQ ID NO: 80) (Milich et al., loc. cit.), on day −28, boosted on day −14 and challenged with $5 \times 10^5$ B16-MUC1-A2K$^b$ cells on day 0. Control mice were given IFA or PBS. A measurable tumour was defined as having a volume greater than 36 mm$^3$.

Results from these experiments are shown in the tables below in the form of the percentage of mice surviving at a given day. For experiments 2 and 3, results using a vaccinia construct that expresses MUC1 (VV-MUC1) are also shown. In other experiments, immunising with MUC1$^{167-175}$ and boosting with MUC1$^{79-87}$, or immunising with MUC1$^{79-87}$ and boosting with MUC1$^{167-175}$, gave a percentage survival of between 60 and 70% at day 30. Experiment 3 shows results from an experiment in which the mice were inoculated with $8 \times 10^5$ A2K$^b$ dendritic cells (DC) which had been pulsed with the peptides.

| Experiment 1 | | | | | | | |
|---|---|---|---|---|---|---|---|
| Day | 0 | 21 | 22 | 23 | 26 | 32 | 34 |
| IFA | 100 | 38 | 0 | 0 | 0 | 0 | 0 |
| MUC1$^{264-272}$ | 100 | 75 | 75 | 75 | 63 | 63 | 63 |
| MUC1$^{167-175}$ | 100 | 63 | 63 | 63 | 63 | 63 | 63 |
| MUC1$^{79-87}$ | 100 | 100 | 75 | 75 | 75 | 75 | 63 |
| MUC1$^{460-468}$ | 100 | 25 | 25 | 25 | 25 | 25 | 25 |
| MUC1$^{13-21}$ | 100 | 25 | 13 | 13 | 0 | 0 | 0 |
| VV-MUC1 | 100 | 75 | 75 | 75 | 63 | 63 | 38 |

| Experiment 2 | | | | | | | | | | |
|---|---|---|---|---|---|---|---|---|---|---|
| Day | 0 | 13 | 24 | 26 | 28 | 33 | 38 | 46 | 52 | 53 |
| IFA | 100 | 100 | 70 | 50 | 50 | 40 | 40 | 30 | 30 | 30 |
| MUC1$^{264-272}$ | 100 | 100 | 100 | 88 | 88 | 75 | 75 | 63 | 63 | 63 |
| MUC1$^{167-175}$ | 100 | 100 | 88 | 63 | 63 | 63 | 63 | 38 | 38 | 38 |
| MUC1$^{79-87}$ | 100 | 100 | 100 | 100 | 100 | 88 | 88 | 75 | 75 | 75 |
| MUC1$^{460-468}$ | 100 | 100 | 100 | 75 | 75 | 50 | 50 | 38 | 38 | 38 |
| MUC1$^{13-21}$ | 100 | 100 | 50 | 25 | 25 | 25 | 25 | 25 | 25 | 25 |
| VV-MUC1 | 100 | 100 | 90 | 80 | 80 | 80 | 80 | 60 | 60 | 60 |

| Experiment 3 | | | | | | | | | | |
|---|---|---|---|---|---|---|---|---|---|---|
| Day | 0 | 15 | 21 | 24 | 27 | 32 | 39 | 40 | 42 | 45 | 72 |
| PBS | 100 | 89 | 56 | 11 | 11 | 11 | 11 | 11 | 11 | 11 | 0 |
| DC + Flu Matrix$^{58-66}$ | 100 | 88 | 63 | 50 | 50 | 38 | 38 | 38 | 38 | 38 | 38 |
| DC + MUC1$^{264-272}$ | 100 | 100 | 88 | 88 | 88 | 88 | 88 | 88 | 88 | 88 | 88 |
| DC + MUC1$^{167-175}$ | 100 | 100 | 78 | 78 | 78 | 78 | 78 | 78 | 67 | 67 | 67 |
| DC + MUC1$^{79-87}$ | 100 | 100 | 89 | 89 | 89 | 67 | 67 | 67 | 67 | 67 | 67 |
| DC + MUC1$^{460-468}$ | 100 | 100 | 75 | 63 | 38 | 38 | 25 | 25 | 25 | 13 | 13 |
| DC + MUC1$^{13-21}$ | 100 | 100 | 67 | 56 | 56 | 44 | 22 | 22 | 22 | 22 | 22 |

The invention claimed is:

1. A method of identifying a MHC class I restricted T cell response, said method comprising contacting a population of cells comprising MHC class I restricted T cells with:
   a polypeptide consisting of SEQ ID NO: 29, and
   determining whether the MHC class I restricted T cells recognize the polypeptide, recognition by the MHC class I restricted T cells indicating the presence of a MHC class I restricted T cell response.

2. The method of claim 1, in which the determination of the MHC class I restricted T cell recognition is done by detecting the expression of a substance by the MHC class I restricted T cells, the expression of the substance indicating that the MHC class I restricted T cells have recognized the polypeptide.

3. The method of claim 2, wherein the substance is IFN-γ.

* * * * *

SEQUENCE LISTING

<160> NUMBER OF SEQ ID NOS: 80

<210> SEQ ID NO 1
<211> LENGTH: 1572
<212> TYPE: DNA
<213> ORGANISM: Homo sapiens
<220> FEATURE:
<221> NAME/KEY: CDS
<222> LOCATION: (58)..(1542)

<400> SEQUENCE: 1

```
gaattccctg gctgcttgaa tctgttctgc ccctcccca cccatttcac caccacc        57 atg aca ccg ggc acc cag tct cct ttc ttc ctg ctg ctc ctc aca       105
Met Thr Pro Gly Thr Gln Ser Pro Phe Phe Leu Leu Leu Leu Thr
 1               5                  10                  15 gtg ctt aca gtt gtt aca ggt tct ggt cat gca agc tct acc cca ggt    153
Val Leu Thr Val Val Thr Gly Ser Gly His Ala Ser Ser Thr Pro Gly
                20                  25                  30 gga gaa aag gag act tcg gct acc cag aga agt tca gtg ccc agc tct    201
Gly Glu Lys Glu Thr Ser Ala Thr Gln Arg Ser Ser Val Pro Ser Ser
             35                  40                  45 act gag aag aat gct gtg agt atg acc agc agc gta ctc tcc agc cac    249
```

```
                Thr Glu Lys Asn Ala Val Ser Met Thr Ser Ser Val Leu Ser Ser His
                    50                  55                  60 agc ccc ggt tca ggc tcc tcc acc act cag gga cag gat gtc act ctg      297
Ser Pro Gly Ser Gly Ser Ser Thr Thr Gln Gly Gln Asp Val Thr Leu
 65                  70                  75                  80 gcc ccg gcc acg gaa cca gct tca ggt tca gct gcc acc tgg gga cag      345
Ala Pro Ala Thr Glu Pro Ala Ser Gly Ser Ala Ala Thr Trp Gly Gln
                     85                  90                  95 gat gtc acc tcg gtc cca gtc acc agg cca gcc ctg ggc tcc acc acc      393
Asp Val Thr Ser Val Pro Val Thr Arg Pro Ala Leu Gly Ser Thr Thr
                100                 105                 110 ccg cca gcc cac gat gtc acc tca gcc ccg gac aac aag cca gcc ccg      441
Pro Pro Ala His Asp Val Thr Ser Ala Pro Asp Asn Lys Pro Ala Pro
                115                 120                 125 ggc tcc acc gcc ccc ccg gcc cac ggt gtc acc tcg gcc ccg gac acc      489
Gly Ser Thr Ala Pro Pro Ala His Gly Val Thr Ser Ala Pro Asp Thr
    130                 135                 140 agg ccg ccc ccg ggc tcc acc gcc ccc gcc gcc cac ggt gtc acc tcg      537
Arg Pro Pro Pro Gly Ser Thr Ala Pro Ala Ala His Gly Val Thr Ser
145                 150                 155                 160 gcc ccg gac acc agg ccg gcc ccg ggc tcc acc gcc ccc ccg gcc cac      585
Ala Pro Asp Thr Arg Pro Ala Pro Gly Ser Thr Ala Pro Pro Ala His
                165                 170                 175 ggt gtc acc tcg gcc ccg gac aac agg ccg gcc ttg ggc tcc acc gcc      633
Gly Val Thr Ser Ala Pro Asp Asn Arg Pro Ala Leu Gly Ser Thr Ala
                180                 185                 190 cct cca gtc cac aat gtc acc tcg gcc tca ggc tct gca tca ggc tca      681
Pro Pro Val His Asn Val Thr Ser Ala Ser Gly Ser Ala Ser Gly Ser
                195                 200                 205 gct tct act ctg gtg cac aac ggc acc tct gcc agg gct acc aca acc      729
Ala Ser Thr Leu Val His Asn Gly Thr Ser Ala Arg Ala Thr Thr Thr
            210                 215                 220 cca gcc agc aag agc act cca ccc agc att ccc agc cac cac tct gat      777
Pro Ala Ser Lys Ser Thr Pro Pro Ser Ile Pro Ser His His Ser Asp
225                 230                 235                 240 act cct acc acc ctt gcc agc cat agc acc aag act gat gcc agt agc      825
Thr Pro Thr Thr Leu Ala Ser His Ser Thr Lys Thr Asp Ala Ser Ser
                245                 250                 255 act cac cat agc acg gta cct cct ctc acc tcc tcc aat cac agc act      873
Thr His His Ser Thr Val Pro Pro Leu Thr Ser Ser Asn His Ser Thr
                260                 265                 270 tct ccc cag ttg tct act ggg gtc tct ttc ttt ttc ctg tct ttt cac      921
Ser Pro Gln Leu Ser Thr Gly Val Ser Phe Phe Phe Leu Ser Phe His
                275                 280                 285 att tca aac ctc cag ttt aat tcc tct ctg gaa gat ccc agc acc gac      969
Ile Ser Asn Leu Gln Phe Asn Ser Ser Leu Glu Asp Pro Ser Thr Asp
            290                 295                 300 tac tac caa gag ctg cag aga gac att tct gaa atg ttt ttg cag att     1017
Tyr Tyr Gln Glu Leu Gln Arg Asp Ile Ser Glu Met Phe Leu Gln Ile
305                 310                 315                 320 tat aaa caa ggg ggt ttt ctg ggc ctc tcc aat att aag ttc agg cca     1065
Tyr Lys Gln Gly Gly Phe Leu Gly Leu Ser Asn Ile Lys Phe Arg Pro
                325                 330                 335 gga tct gtg gtg gta caa ttg act ctg gcc ttc cga gaa ggt acc atc     1113
Gly Ser Val Val Val Gln Leu Thr Leu Ala Phe Arg Glu Gly Thr Ile
                340                 345                 350 aat gtc cac gac gtg gag aca cag ttc aat cag tat aaa acg gaa gca     1161
Asn Val His Asp Val Glu Thr Gln Phe Asn Gln Tyr Lys Thr Glu Ala
                355                 360                 365
```

```
gcc tct cga tat aac ctg acg atc tca gac gtc agc gtg agt cat gtg     1209
Ala Ser Arg Tyr Asn Leu Thr Ile Ser Asp Val Ser Val Ser His Val
    370                 375                 380 cca ttt cct ttc tct gcc cag tct ggg gct ggg gtg cca ggc tgg ggc     1257
Pro Phe Pro Phe Ser Ala Gln Ser Gly Ala Gly Val Pro Gly Trp Gly
385                 390                 395                 400 atc gcg ctg ctg gtg ctg gtc tgt gtt ctg gtt gcg ctg gcc att gtc     1305
Ile Ala Leu Leu Val Leu Val Cys Val Leu Val Ala Leu Ala Ile Val
                405                 410                 415 tat ctc att gcc ttg gct gtc tgt cag tgc cgc cga aag aac tac ggg     1353
Tyr Leu Ile Ala Leu Ala Val Cys Gln Cys Arg Arg Lys Asn Tyr Gly
            420                 425                 430 cag ctg gac atc ttt cca gcc cgg gat acc tac cat cct atg agc gag     1401
Gln Leu Asp Ile Phe Pro Ala Arg Asp Thr Tyr His Pro Met Ser Glu
        435                 440                 445 tac ccc acc tac cac acc cat ggg cgc tat gtg ccc cct agc agt acc     1449
Tyr Pro Thr Tyr His Thr His Gly Arg Tyr Val Pro Pro Ser Ser Thr
    450                 455                 460 gat cgt agc ccc tat gag aag gtt tct gca ggt aat ggt ggc agc agc     1497
Asp Arg Ser Pro Tyr Glu Lys Val Ser Ala Gly Asn Gly Gly Ser Ser
465                 470                 475                 480 ctc tct tac aca aac cca gca gtg gca gcc act tct gcc aac ttg           1542
Leu Ser Tyr Thr Asn Pro Ala Val Ala Ala Thr Ser Ala Asn Leu
                485                 490                 495 tagggcacg tcgccctctg agctgagtgg                                      1572

<210> SEQ ID NO 2
<211> LENGTH: 495
<212> TYPE: PRT
<213> ORGANISM: Homo sapiens

<400> SEQUENCE: 2

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
                20                  25                  30

Gly Glu Lys Glu Thr Ser Ala Thr Gln Arg Ser Ser Val Pro Ser Ser
            35                  40                  45

Thr Glu Lys Asn Ala Val Ser Met Thr Ser Ser Val Leu Ser Ser His
        50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
        115                 120                 125

Gly Ser Thr Ala Pro Pro Ala His Gly Val Thr Ser Ala Pro Asp Thr
130                 135                 140

Arg Pro Pro Gly Ser Thr Ala Pro Ala Ala His Gly Val Thr Ser
145                 150                 155                 160

Ala Pro Asp Thr Arg Pro Ala Pro Gly Ser Thr Ala Pro Pro Ala His
                165                 170                 175

Gly Val Thr Ser Ala Pro Asp Asn Arg Pro Ala Leu Gly Ser Thr Ala
            180                 185                 190

Pro Pro Val His Asn Val Thr Ser Ala Ser Gly Ser Ala Ser Gly Ser
```

-continued

```
                195                 200                 205
Ala Ser Thr Leu Val His Asn Gly Thr Ser Ala Arg Ala Thr Thr Thr
    210                 215                 220
Pro Ala Ser Lys Ser Thr Pro Pro Ser Ile Pro Ser His His Ser Asp
225                 230                 235                 240
Thr Pro Thr Thr Leu Ala Ser His Ser Thr Lys Thr Asp Ala Ser Ser
                245                 250                 255
Thr His His Ser Thr Val Pro Pro Leu Thr Ser Ser Asn His Ser Thr
            260                 265                 270
Ser Pro Gln Leu Ser Thr Gly Val Ser Phe Phe Leu Ser Phe His
        275                 280                 285
Ile Ser Asn Leu Gln Phe Asn Ser Ser Leu Glu Asp Pro Ser Thr Asp
290                 295                 300
Tyr Tyr Gln Glu Leu Gln Arg Asp Ile Ser Glu Met Phe Leu Gln Ile
305                 310                 315                 320
Tyr Lys Gln Gly Gly Phe Leu Gly Leu Ser Asn Ile Lys Phe Arg Pro
                325                 330                 335
Gly Ser Val Val Val Gln Leu Thr Leu Ala Phe Arg Glu Gly Thr Ile
            340                 345                 350
Asn Val His Asp Val Glu Thr Gln Phe Asn Gln Tyr Lys Thr Glu Ala
        355                 360                 365
Ala Ser Arg Tyr Asn Leu Thr Ile Ser Asp Val Ser Val Ser His Val
    370                 375                 380
Pro Phe Pro Phe Ser Ala Gln Ser Gly Ala Gly Val Pro Gly Trp Gly
385                 390                 395                 400
Ile Ala Leu Leu Val Leu Val Cys Val Leu Val Ala Leu Ala Ile Val
                405                 410                 415
Tyr Leu Ile Ala Leu Ala Val Cys Gln Cys Arg Arg Lys Asn Tyr Gly
            420                 425                 430
Gln Leu Asp Ile Phe Pro Ala Arg Asp Thr Tyr His Pro Met Ser Glu
        435                 440                 445
Tyr Pro Thr Tyr His Thr His Gly Arg Tyr Val Pro Pro Ser Ser Thr
    450                 455                 460
Asp Arg Ser Pro Tyr Glu Lys Val Ser Ala Gly Asn Gly Gly Ser Ser
465                 470                 475                 480
Leu Ser Tyr Thr Asn Pro Ala Val Ala Ala Thr Ser Ala Asn Leu
                485                 490                 495

<210> SEQ ID NO 3
<211> LENGTH: 9
<212> TYPE: PRT
<213> ORGANISM: Homo sapiens
<220> FEATURE:
<221> NAME/KEY: CDS
<222> LOCATION: (58)..(1542)

<400> SEQUENCE: 3

Ala Leu Gly Ser Thr Ala Pro Pro Val
 1               5

<210> SEQ ID NO 4
<211> LENGTH: 9
<212> TYPE: PRT
<213> ORGANISM: Homo sapiens

<400> SEQUENCE: 4

Phe Leu Ser Phe His Ile Ser Asn Leu
```

```
<210> SEQ ID NO 5
<211> LENGTH: 9
<212> TYPE: PRT
<213> ORGANISM: Homo sapiens

<400> SEQUENCE: 5

Thr Leu Ala Pro Ala Thr Glu Pro Ala
1               5

<210> SEQ ID NO 6
<211> LENGTH: 9
<212> TYPE: PRT
<213> ORGANISM: Homo sapiens

<400> SEQUENCE: 6

Ser Leu Ser Tyr Thr Asn Pro Ala Val
1               5

<210> SEQ ID NO 7
<211> LENGTH: 9
<212> TYPE: PRT
<213> ORGANISM: Homo sapiens

<400> SEQUENCE: 7

Ser Val Pro Val Thr Arg Pro Ala Leu
1               5

<210> SEQ ID NO 8
<211> LENGTH: 9
<212> TYPE: PRT
<213> ORGANISM: Homo sapiens

<400> SEQUENCE: 8

Gly Val Pro Gly Trp Gly Ile Ala Leu
1               5

<210> SEQ ID NO 9
<211> LENGTH: 9
<212> TYPE: PRT
<213> ORGANISM: Homo sapiens

<400> SEQUENCE: 9

Ala Pro Gly Ser Thr Ala Pro Pro Ala
1               5

<210> SEQ ID NO 10
<211> LENGTH: 9
<212> TYPE: PRT
<213> ORGANISM: Homo sapiens

<400> SEQUENCE: 10

Ala Val Ser Met Thr Ser Ser Val Leu
1               5

<210> SEQ ID NO 11
<211> LENGTH: 9
<212> TYPE: PRT
<213> ORGANISM: Homo sapiens

<400> SEQUENCE: 11

Ala Val Ala Ala Thr Ser Ala Asn Leu
1               5
```

```
<210> SEQ ID NO 12
<211> LENGTH: 9
<212> TYPE: PRT
<213> ORGANISM: Homo sapiens

<400> SEQUENCE: 12

Arg Pro Gly Ser Val Val Val Gln Leu
1               5

<210> SEQ ID NO 13
<211> LENGTH: 9
<212> TYPE: PRT
<213> ORGANISM: Homo sapiens

<400> SEQUENCE: 13

Val Pro Gly Trp Gly Ile Ala Leu Leu
1               5

<210> SEQ ID NO 14
<211> LENGTH: 9
<212> TYPE: PRT
<213> ORGANISM: Homo sapiens

<400> SEQUENCE: 14

Ser Ala Ser Gly Ser Ala Ser Thr Leu
1               5

<210> SEQ ID NO 15
<211> LENGTH: 9
<212> TYPE: PRT
<213> ORGANISM: Homo sapiens

<400> SEQUENCE: 15

Ser Ala Gly Asn Gly Gly Ser Ser Leu
1               5

<210> SEQ ID NO 16
<211> LENGTH: 9
<212> TYPE: PRT
<213> ORGANISM: Homo sapiens

<400> SEQUENCE: 16

Ala Leu Ala Val Cys Gln Cys Arg Arg
1               5

<210> SEQ ID NO 17
<211> LENGTH: 9
<212> TYPE: PRT
<213> ORGANISM: Homo sapiens

<400> SEQUENCE: 17

Gly Gln Leu Asp Ile Phe Pro Ala Arg
1               5

<210> SEQ ID NO 18
<211> LENGTH: 10
<212> TYPE: PRT
<213> ORGANISM: Homo sapiens

<400> SEQUENCE: 18

Thr Leu Val His Asn Gly Thr Ser Ala Arg
1               5                   10

<210> SEQ ID NO 19
```

```
<211> LENGTH: 9
<212> TYPE: PRT
<213> ORGANISM: Homo sapiens

<400> SEQUENCE: 19

Thr Thr Leu Ala Ser His Ser Thr Lys
 1               5

<210> SEQ ID NO 20
<211> LENGTH: 9
<212> TYPE: PRT
<213> ORGANISM: Homo sapiens

<400> SEQUENCE: 20

Gly Val Thr Ser Ala Pro Asp Thr Arg
 1               5

<210> SEQ ID NO 21
<211> LENGTH: 9
<212> TYPE: PRT
<213> ORGANISM: Homo sapiens

<400> SEQUENCE: 21

Gly Val Thr Ser Ala Pro Asp Asn Arg
 1               5

<210> SEQ ID NO 22
<211> LENGTH: 10
<212> TYPE: PRT
<213> ORGANISM: Homo sapiens

<400> SEQUENCE: 22

Ile Tyr Lys Gln Gly Gly Phe Leu Gly Leu
 1               5                  10

<210> SEQ ID NO 23
<211> LENGTH: 10
<212> TYPE: PRT
<213> ORGANISM: Homo sapiens

<400> SEQUENCE: 23

Phe Phe Leu Ser Phe His Ile Ser Asn Leu
 1               5                  10

<210> SEQ ID NO 24
<211> LENGTH: 10
<212> TYPE: PRT
<213> ORGANISM: Homo sapiens
<220> FEATURE:
<221> NAME/KEY: CDS
<222> LOCATION: (58)..(1542)

<400> SEQUENCE: 24

Gly Phe Leu Gly Leu Ser Asn Ile Lys Phe
 1               5                  10

<210> SEQ ID NO 25
<211> LENGTH: 10
<212> TYPE: PRT
<213> ORGANISM: Homo sapiens

<400> SEQUENCE: 25

Tyr Tyr Gln Glu Leu Gln Arg Asp Ile Ser
 1               5                  10
```

-continued

```
<210> SEQ ID NO 26
<211> LENGTH: 9
<212> TYPE: PRT
<213> ORGANISM: Homo sapiens

<400> SEQUENCE: 26

Ile Ser Glu Met Phe Leu Gln Ile Tyr
1               5

<210> SEQ ID NO 27
<211> LENGTH: 9
<212> TYPE: PRT
<213> ORGANISM: Homo sapiens

<400> SEQUENCE: 27

Asp Val Glu Thr Gln Phe Asn Gln Tyr
1               5

<210> SEQ ID NO 28
<211> LENGTH: 10
<212> TYPE: PRT
<213> ORGANISM: Homo sapiens

<400> SEQUENCE: 28

Ser Leu Glu Asp Pro Ser Thr Asp Tyr Tyr
1               5                   10

<210> SEQ ID NO 29
<211> LENGTH: 10
<212> TYPE: PRT
<213> ORGANISM: Homo sapiens

<400> SEQUENCE: 29

Ile Ser Glu Met Phe Leu Gln Ile Tyr Lys
1               5                   10

<210> SEQ ID NO 30
<211> LENGTH: 9
<212> TYPE: PRT
<213> ORGANISM: Homo sapiens

<400> SEQUENCE: 30

Asn Ile Lys Phe Arg Pro Gly Ser Val
1               5

<210> SEQ ID NO 31
<211> LENGTH: 9
<212> TYPE: PRT
<213> ORGANISM: Homo sapiens

<400> SEQUENCE: 31

Thr Leu Ala Phe Arg Glu Gly Thr Ile
1               5

<210> SEQ ID NO 32
<211> LENGTH: 10
<212> TYPE: PRT
<213> ORGANISM: Homo sapiens

<400> SEQUENCE: 32

Gln Cys Arg Arg Lys Asn Tyr Gly Gln Leu
1               5                   10

<210> SEQ ID NO 33
<211> LENGTH: 9
```

```
<212> TYPE: PRT
<213> ORGANISM: Homo sapiens

<400> SEQUENCE: 33

Glu Ala Ala Ser Arg Tyr Asn Leu Thr
 1               5

<210> SEQ ID NO 34
<211> LENGTH: 27
<212> TYPE: DNA
<213> ORGANISM: Homo sapiens

<400> SEQUENCE: 34
gccttgggct ccaccgcccc tccagtc                                        27

<210> SEQ ID NO 35
<211> LENGTH: 27
<212> TYPE: DNA
<213> ORGANISM: Homo sapiens

<400> SEQUENCE: 35
ttcctgtctt ttcacatttc aaacctc                                        27

<210> SEQ ID NO 36
<211> LENGTH: 27
<212> TYPE: DNA
<213> ORGANISM: Homo sapiens

<400> SEQUENCE: 36
actctggccc cggccacgga accagct                                        27

<210> SEQ ID NO 37
<211> LENGTH: 27
<212> TYPE: DNA
<213> ORGANISM: Homo sapiens

<400> SEQUENCE: 37
agcctctctt acacaaaccc agcagtg                                        27

<210> SEQ ID NO 38
<211> LENGTH: 27
<212> TYPE: DNA
<213> ORGANISM: Homo sapiens

<400> SEQUENCE: 38
tcggtcccag tcaccaggcc agccctg                                        27

<210> SEQ ID NO 39
<211> LENGTH: 27
<212> TYPE: DNA
<213> ORGANISM: Homo sapiens

<400> SEQUENCE: 39
ggggtgccag gctggggcat cgcgctg                                        27

<210> SEQ ID NO 40
<211> LENGTH: 27
<212> TYPE: DNA
<213> ORGANISM: Homo sapiens

<400> SEQUENCE: 40
gccccgggct ccaccgcccc cccggcc                                        27
```

```
<210> SEQ ID NO 41
<211> LENGTH: 27
<212> TYPE: DNA
<213> ORGANISM: Homo sapiens

<400> SEQUENCE: 41
gctgtgagta tgaccagcag cgtactc                                          27

<210> SEQ ID NO 42
<211> LENGTH: 27
<212> TYPE: DNA
<213> ORGANISM: Homo sapiens

<400> SEQUENCE: 42
gcagtggcag ccacttctgc caacttg                                          27

<210> SEQ ID NO 43
<211> LENGTH: 27
<212> TYPE: DNA
<213> ORGANISM: Homo sapiens

<400> SEQUENCE: 43
aggccaggat ctgtggtggt acaattg                                          27

<210> SEQ ID NO 44
<211> LENGTH: 27
<212> TYPE: DNA
<213> ORGANISM: Homo sapiens

<400> SEQUENCE: 44
gtgccaggct ggggcatcgc gctgctg                                          27

<210> SEQ ID NO 45
<211> LENGTH: 27
<212> TYPE: DNA
<213> ORGANISM: Homo sapiens

<400> SEQUENCE: 45
tctgcatcag gctcagcttc tactctg                                          27

<210> SEQ ID NO 46
<211> LENGTH: 27
<212> TYPE: DNA
<213> ORGANISM: Homo sapiens

<400> SEQUENCE: 46
tctgcaggta atggtggcag cagcctc                                          27

<210> SEQ ID NO 47
<211> LENGTH: 27
<212> TYPE: DNA
<213> ORGANISM: Homo sapiens

<400> SEQUENCE: 47
gccttggctg tctgtcagtg ccgccga                                          27

<210> SEQ ID NO 48
<211> LENGTH: 27
<212> TYPE: DNA
<213> ORGANISM: Homo sapiens

<400> SEQUENCE: 48
gggcagctgg acatctttcc agcccgg                                          27
```

```
<210> SEQ ID NO 49
<211> LENGTH: 30
<212> TYPE: DNA
<213> ORGANISM: Homo sapiens

<400> SEQUENCE: 49
actctggtgc acaacggcac ctctgccagg                                      30

<210> SEQ ID NO 50
<211> LENGTH: 27
<212> TYPE: DNA
<213> ORGANISM: Homo sapiens

<400> SEQUENCE: 50
accacccttg ccagccatag caccaag                                         27

<210> SEQ ID NO 51
<211> LENGTH: 27
<212> TYPE: DNA
<213> ORGANISM: Homo sapiens

<400> SEQUENCE: 51
ggtgtcacct cggccccgga caccagg                                         27

<210> SEQ ID NO 52
<211> LENGTH: 27
<212> TYPE: DNA
<213> ORGANISM: Homo sapiens

<400> SEQUENCE: 52
ggtgtcacct cggccccgga caacagg                                         27

<210> SEQ ID NO 53
<211> LENGTH: 30
<212> TYPE: DNA
<213> ORGANISM: Homo sapiens

<400> SEQUENCE: 53
atttataaac aaggggtttt tctgggcctc                                      30

<210> SEQ ID NO 54
<211> LENGTH: 30
<212> TYPE: DNA
<213> ORGANISM: Homo sapiens

<400> SEQUENCE: 54
tttttcctgt cttttcacat ttcaaacctc                                      30

<210> SEQ ID NO 55
<211> LENGTH: 30
<212> TYPE: DNA
<213> ORGANISM: Homo sapiens

<400> SEQUENCE: 55
ggttttctgg gcctctccaa tattaagttc                                      30

<210> SEQ ID NO 56
<211> LENGTH: 30
<212> TYPE: DNA
<213> ORGANISM: Homo sapiens

<400> SEQUENCE: 56
tactaccaag agctgcagag agacatttct                                      30
```

<210> SEQ ID NO 57
<211> LENGTH: 27
<212> TYPE: DNA
<213> ORGANISM: Homo sapiens

<400> SEQUENCE: 57
atttctgaaa tgttttttgca gatttat                              27

<210> SEQ ID NO 58
<211> LENGTH: 30
<212> TYPE: DNA
<213> ORGANISM: Homo sapiens

<400> SEQUENCE: 58
atttctgaaa tgttttttgca gatttataaa                           30

<210> SEQ ID NO 59
<211> LENGTH: 30
<212> TYPE: DNA
<213> ORGANISM: Homo sapiens

<400> SEQUENCE: 59
tctctggaag atcccagcac cgactactac                            30

<210> SEQ ID NO 60
<211> LENGTH: 27
<212> TYPE: DNA
<213> ORGANISM: Homo sapiens

<400> SEQUENCE: 60
gacgtggaga cacagttcaa tcagtat                               27

<210> SEQ ID NO 61
<211> LENGTH: 27
<212> TYPE: DNA
<213> ORGANISM: Homo sapiens

<400> SEQUENCE: 61
aatattaagt tcaggccagg atctgtg                               27

<210> SEQ ID NO 62
<211> LENGTH: 27
<212> TYPE: DNA
<213> ORGANISM: Homo sapiens

<400> SEQUENCE: 62
actctggcct tccgagaagg taccatc                               27

<210> SEQ ID NO 63
<211> LENGTH: 30
<212> TYPE: DNA
<213> ORGANISM: Homo sapiens

<400> SEQUENCE: 63
cagtgccgcc gaaagaacta cgggcagctg                            30

<210> SEQ ID NO 64
<211> LENGTH: 27
<212> TYPE: DNA
<213> ORGANISM: Homo sapiens

<400> SEQUENCE: 64

-continued gaagcagcct ctcgatataa cctgacg                          27

<210> SEQ ID NO 65
<211> LENGTH: 9
<212> TYPE: PRT
<213> ORGANISM: Homo sapiens

<400> SEQUENCE: 65

Leu Leu Leu Thr Val Leu Thr Val Val
1               5

<210> SEQ ID NO 66
<211> LENGTH: 9
<212> TYPE: PRT
<213> ORGANISM: Homo sapiens

<400> SEQUENCE: 66

Ala Leu Gly Ser Thr Thr Pro Pro Ala
1               5

<210> SEQ ID NO 67
<211> LENGTH: 475
<212> TYPE: PRT
<213> ORGANISM: Homo sapiens

<400> SEQUENCE: 1

Met Thr Pro Gly Thr Gln Ser Pro Phe Phe Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Val Ser Met Thr Ser Ser Val Leu Ser Ser His
    50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
        115                 120                 125

Gly Ser Thr Ala Pro Pro Ala His Gly Val Thr Ser Ala Pro Asp Thr
    130                 135                 140

Arg Pro Ala Pro Gly Ser Thr Ala Pro Pro Ala His Gly Val Thr Ser
145                 150                 155                 160

Ala Pro Asp Asn Arg Pro Ala Leu Gly Ser Thr Ala Pro Pro Val His
                165                 170                 175

Asn Val Thr Ser Ala Ser Gly Ser Ala Ser Gly Ser Ala Ser Thr Leu
            180                 185                 190

Val His Asn Gly Thr Ser Ala Arg Ala Thr Thr Thr Pro Ala Ser Lys
        195                 200                 205

Ser Thr Pro Phe Ser Ile Pro Ser His His Ser Asp Thr Pro Thr Thr
    210                 215                 220

Leu Ala Ser His Ser Thr Lys Thr Asp Ala Ser Ser Thr His His Ser
225                 230                 235                 240

Thr Val Pro Pro Leu Thr Ser Ser Asn His Ser Thr Ser Pro Gln Leu
                245                 250                 255

```
Ser Thr Gly Val Ser Phe Phe Leu Ser Phe His Ile Ser Asn Leu
            260                 265                 270

Gln Phe Asn Ser Ser Leu Glu Asp Pro Ser Thr Asp Tyr Tyr Gln Glu
        275                 280                 285

Leu Gln Arg Asp Ile Ser Glu Met Phe Leu Gln Ile Tyr Lys Gln Gly
    290                 295                 300

Gly Phe Leu Gly Leu Ser Asn Ile Lys Phe Arg Pro Gly Ser Val Val
305                 310                 315                 320

Val Gln Leu Thr Leu Ala Phe Arg Glu Gly Thr Ile Asn Val His Asp
                325                 330                 335

Val Glu Thr Gln Phe Asn Gln Tyr Lys Thr Glu Ala Ala Ser Arg Tyr
            340                 345                 350

Asn Leu Thr Ile Ser Asp Val Ser Val Ser Asp Val Pro Phe Pro Phe
        355                 360                 365

Ser Ala Gln Ser Gly Ala Gly Val Pro Gly Trp Gly Ile Ala Leu Leu
    370                 375                 380

Val Leu Val Cys Val Leu Val Ala Leu Ala Ile Val Tyr Leu Ile Ala
385                 390                 395                 400

Leu Ala Val Cys Gln Cys Arg Arg Lys Asn Tyr Gly Gln Leu Asp Ile
                405                 410                 415

Phe Pro Ala Arg Asp Thr Tyr His Pro Met Ser Glu Tyr Pro Thr Tyr
            420                 425                 430

His Thr His Gly Arg Tyr Val Pro Pro Ser Ser Thr Asp Arg Ser Pro
        435                 440                 445

Tyr Glu Lys Val Ser Ala Gly Asn Gly Gly Ser Ser Leu Ser Tyr Thr
    450                 455                 460

Asn Pro Ala Val Ala Ala Thr Ser Ala Asn Leu
465                 470                 475

<210> SEQ ID NO 68
<211> LENGTH: 9
<212> TYPE: PRT
<213> ORGANISM: Homo sapiens

<400> SEQUENCE: 68

Tyr Leu Glu Pro Ala Cys Ala Lys Tyr
1               5

<210> SEQ ID NO 69
<211> LENGTH: 10
<212> TYPE: PRT
<213> ORGANISM: Homo sapiens

<400> SEQUENCE: 69

Phe Leu Pro Ser Asp Cys Phe Pro Ser Val
1               5                   10

<210> SEQ ID NO 70
<211> LENGTH: 10
<212> TYPE: PRT
<213> ORGANISM: Homo sapiens

<400> SEQUENCE: 70

Lys Val Phe Pro Cys Ala Leu Ile Asn Lys
1               5                   10

<210> SEQ ID NO 71
<211> LENGTH: 9
```

```
<212> TYPE: PRT
<213> ORGANISM: Homo sapiens

<400> SEQUENCE: 71

Arg Tyr Leu Lys Cys Gln Gln Leu Leu
1               5

<210> SEQ ID NO 72
<211> LENGTH: 10
<212> TYPE: PRT
<213> ORGANISM: Homo sapiens

<400> SEQUENCE: 72

Ala Pro Ala Pro Ala Pro Cys Trp Pro Leu
1               5                   10

<210> SEQ ID NO 73
<211> LENGTH: 9
<212> TYPE: PRT
<213> ORGANISM: Homo sapiens

<400> SEQUENCE: 73

Phe Leu Arg Gly Arg Ala Cys Gly Ile
1               5

<210> SEQ ID NO 74
<211> LENGTH: 9
<212> TYPE: PRT
<213> ORGANISM: Homo sapiens

<400> SEQUENCE: 74

Cys Thr Glu Leu Lys Leu Ser Asp Tyr
1               5

<210> SEQ ID NO 75
<211> LENGTH: 9
<212> TYPE: PRT
<213> ORGANISM: Homo sapiens

<400> SEQUENCE: 75

Gly Ile Leu Gly Phe Val Phe Thr Leu
1               5

<210> SEQ ID NO 76
<211> LENGTH: 9
<212> TYPE: PRT
<213> ORGANISM: Homo sapiens

<400> SEQUENCE: 76

Gln Val Pro Leu Arg Pro Met Tyr Lys
1               5

<210> SEQ ID NO 77
<211> LENGTH: 9
<212> TYPE: PRT
<213> ORGANISM: Homo sapiens

<400> SEQUENCE: 77

Ala Tyr Gly Leu Asp Phe Tyr Ile Leu
1               5

<210> SEQ ID NO 78
<211> LENGTH: 9
<212> TYPE: PRT
<213> ORGANISM: Homo sapiens
```

```
-continued

<400> SEQUENCE: 78

Arg Pro Pro Ile Phe Ile Arg Arg Leu
 1               5

<210> SEQ ID NO 79
<211> LENGTH: 8
<212> TYPE: PRT
<213> ORGANISM: Homo sapiens

<400> SEQUENCE: 79

Tyr Leu Tyr Asp Gln Gln Leu Leu
 1               5

<210> SEQ ID NO 80
<211> LENGTH: 13
<212> TYPE: PRT
<213> ORGANISM: Homo sapiens

<400> SEQUENCE: 80

Thr Pro Pro Ala Tyr Arg Pro Pro Asn Ala Pro Ile Leu
 1               5                  10
```